(12) United States Patent
Hibner

(10) Patent No.: US 8,951,207 B2
(45) Date of Patent: Feb. 10, 2015

(54) TETHERLESS BIOPSY DEVICE

(71) Applicant: Devicor Medical Products, Inc., Cincinnati, OH (US)

(72) Inventor: John A. Hibner, Mason, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 0 days.

(21) Appl. No.: 14/097,636

(22) Filed: Dec. 5, 2013

(65) Prior Publication Data

US 2014/0094713 A1    Apr. 3, 2014

Related U.S. Application Data

(63) Continuation of application No. 13/113,198, filed on May 23, 2011, now Pat. No. 8,622,926.

(51) Int. Cl.
*A61B 10/00* (2006.01)
*A61B 10/02* (2006.01)

(52) U.S. Cl.
CPC ......... *A61B 10/0283* (2013.01); *A61B 10/0275* (2013.01); *A61B 10/0266* (2013.01); *A61B 2010/0093* (2013.01); *A61B 2010/0208* (2013.01)
USPC ...................................... 600/565

(58) Field of Classification Search
CPC ........... A61B 10/0283; A61B 10/0275; A61B 10/0266; A61B 2010/0093; A61B 2010/0208
USPC ................................. 600/562–568
See application file for complete search history.

(56) References Cited

U.S. PATENT DOCUMENTS

| | | | |
|---|---|---|---|
| 5,526,822 A | 6/1996 | Burbank et al. |
| 6,086,544 A | 7/2000 | Hibner et al. |
| 6,626,849 B2 | 9/2003 | Huitema et al. |
| 7,442,171 B2 | 10/2008 | Stephens et al. |
| 7,854,706 B2 | 12/2010 | Hibner et al. |
| 7,918,804 B2 | 4/2011 | Monson et al. |
| 8,118,755 B2 | 2/2012 | Hibner et al. |
| 8,157,744 B2 | 4/2012 | Jorgensen et al. |
| 8,177,729 B2 | 5/2012 | Hibner et al. |
| 8,206,316 B2 | 6/2012 | Hibner et al. |
| 8,337,415 B2 | 12/2012 | Trezza, II et al. |

(Continued)

OTHER PUBLICATIONS

International Search Report dated Oct. 29, 2012 for Application No. PCT/US2012/037435.

(Continued)

*Primary Examiner* — Brian Szmal
(74) *Attorney, Agent, or Firm* — Frost Brown Todd LLC

(57) ABSTRACT

A biopsy device comprises a body, a needle, and a cutter operable to sever tissue protruding through a lateral aperture of the needle. A vacuum pump is in fluid communication with the cutter. A fluid pump is in fluid communication with the needle. A fluid pump actuation assembly is operable to actuate the fluid pump to deliver a bolus of fluid to the needle based on movement of the cutter. A valve assembly responsive to cutter movement is operable to selectively couple the needle with the fluid pump, couple the needle with atmospheric air, or seal the needle relative to the fluid pump and atmospheric air. The fluid from the fluid pump and atmospheric air cooperate with the vacuum to urge severed tissue samples proximally through the cutter. Components operable to actuate the cutter and the fluid pump include coaxial lead screws having different pitch diameters.

20 Claims, 30 Drawing Sheets

(56) References Cited

U.S. PATENT DOCUMENTS

| | | |
|---|---|---|
| 2006/0074345 A1 | 4/2006 | Hibner |
| 2008/0214955 A1 | 9/2008 | Speeg et al. |
| 2008/0319341 A1 | 12/2008 | Taylor et al. |
| 2010/0152610 A1 | 6/2010 | Parihar et al. |
| 2010/0160819 A1 | 6/2010 | Parihar et al. |
| 2010/0198066 A1 | 8/2010 | Voegele |
| 2010/0292607 A1 | 11/2010 | Moore et al. |
| 2012/0059247 A1 | 3/2012 | Speeg et al. |
| 2012/0109007 A1 | 5/2012 | Rhad et al. |

OTHER PUBLICATIONS

Provisional U.S. Appl. No. 61/381,466, filed Sep. 10, 2010.

TETHERLESS BIOPSY DEVICE

BACKGROUND

Biopsy samples have been obtained in a variety of ways in various medical procedures using a variety of devices. Biopsy devices may be used under stereotactic guidance, ultrasound guidance, MRI guidance, PEM guidance, BSGI guidance, or otherwise. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device.

Merely exemplary biopsy devices are disclosed in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pub. No. 2003/0109803, entitled "MRI Compatible Surgical Biopsy Device," published Jun. 12, 2003; U.S. Pub. No. 2006/0074345, entitled "Biopsy Apparatus and Method," published Apr. 6, 2006; U.S. Pub. No. 2007/0118048, entitled "Remote Thumbwheel for a Surgical Biopsy Device," published May 24, 2007; U.S. Pub. No. 2008/0214955, entitled "Presentation of Biopsy Sample by Biopsy Device," published Sep. 4, 2008; U.S. Pub. No. 2009/0171242, entitled "Clutch and Valving System for Tetherless Biopsy Device," published Jul. 2, 2009; U.S. Pub. No. 2010/0152610, entitled "Hand Actuated Tetherless Biopsy Device with Pistol Grip," published Jun. 17, 2010; U.S. Pub. No. 2010/0160819, entitled "Biopsy Device with Central Thumbwheel," published Jun. 24, 2010; U.S. Pub. No. 2010/0317997, entitled "Tetherless Biopsy Device with Reusable Portion," published Dec. 16, 2010; and U.S. Non-Provisional patent application Ser. No. 12/953,715, entitled "Handheld Biopsy Device with Needle Firing," filed Nov. 24, 2010. The disclosure of each of the above-cited U.S. patents, U.S. patent application Publications, and U.S. Non-Provisional patent applications is incorporated by reference herein.

While several systems and methods have been made and used for obtaining a biopsy sample, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings. In the drawings, like numerals represent like elements throughout the several views.

Figure 1:
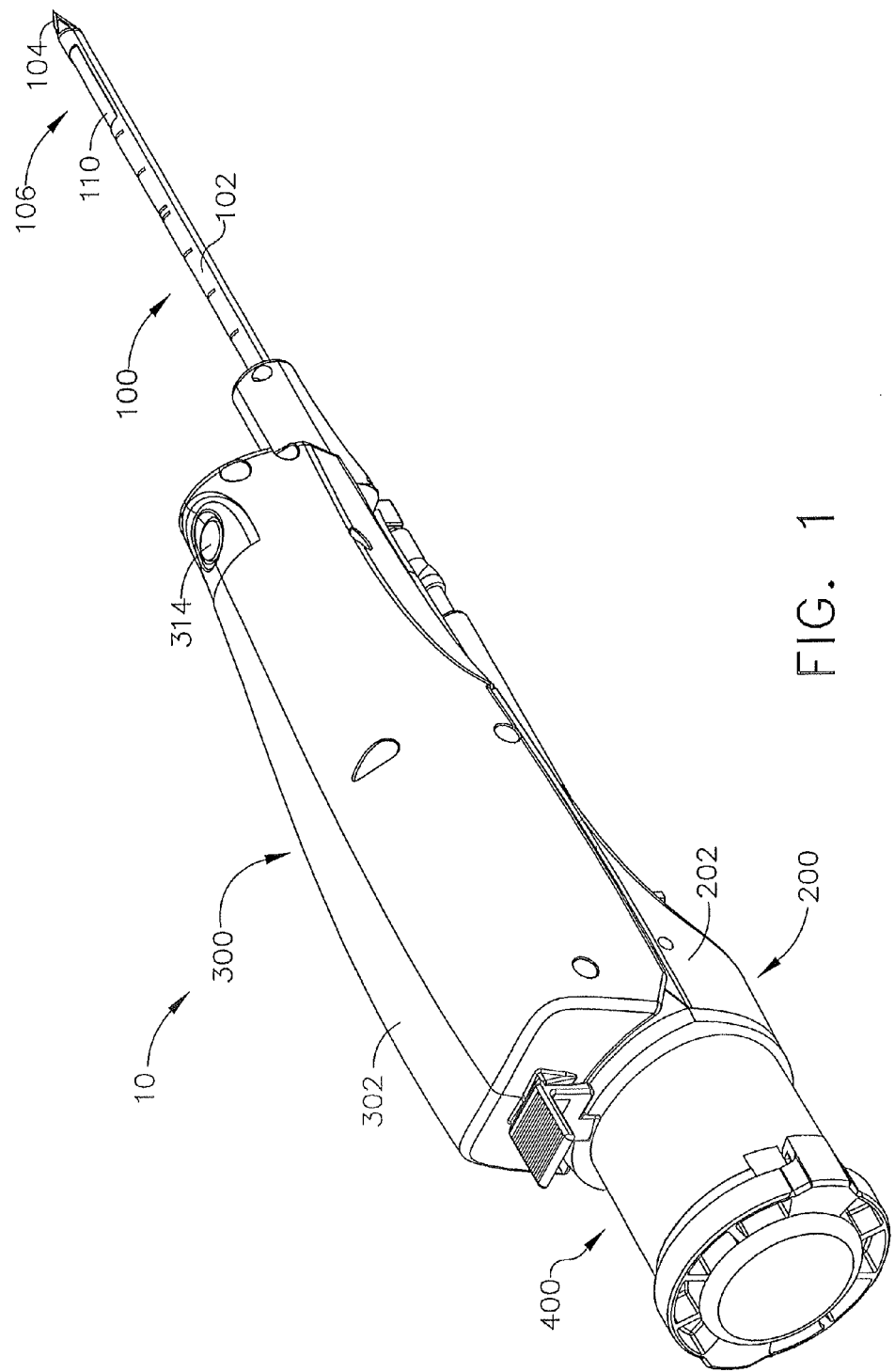
FIG. 1 depicts a perspective view of an exemplary biopsy device.
Figure 2:
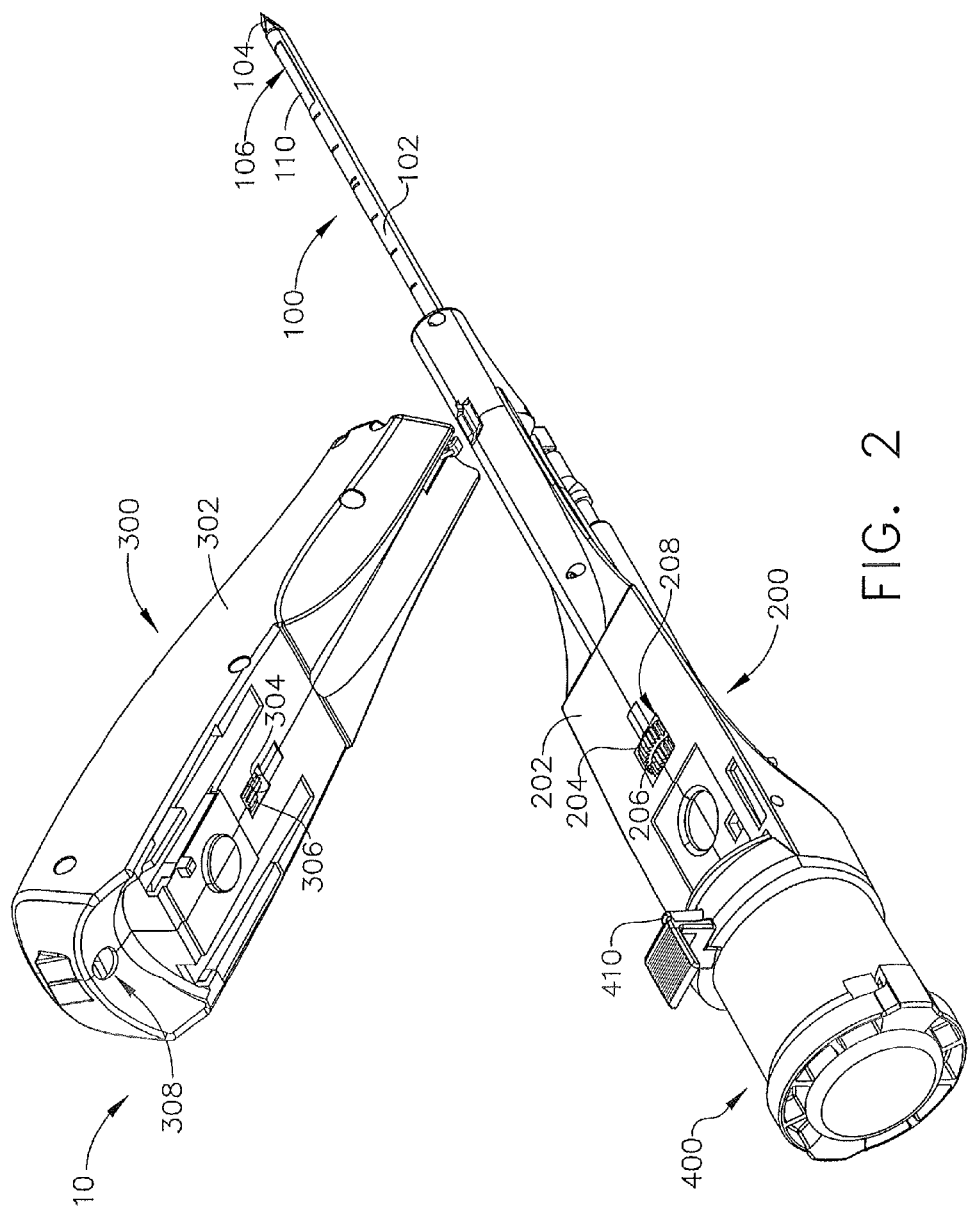
FIG. 2 depicts a perspective view of the biopsy device of FIG. 1, with the probe and holster separated from each other.
Figure 3:
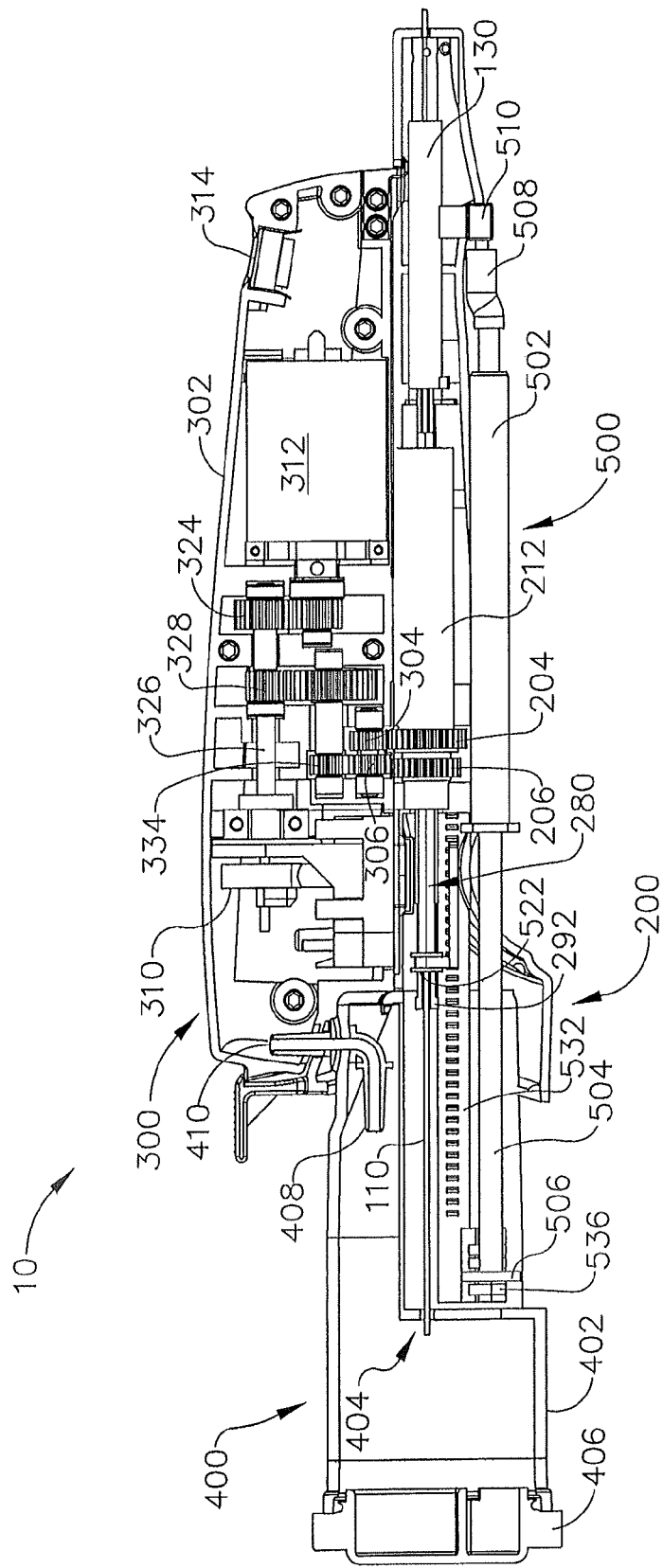
FIG. 3 depicts a partial, side cross-sectional view of the biopsy device of FIG. 1.
Figure 4:
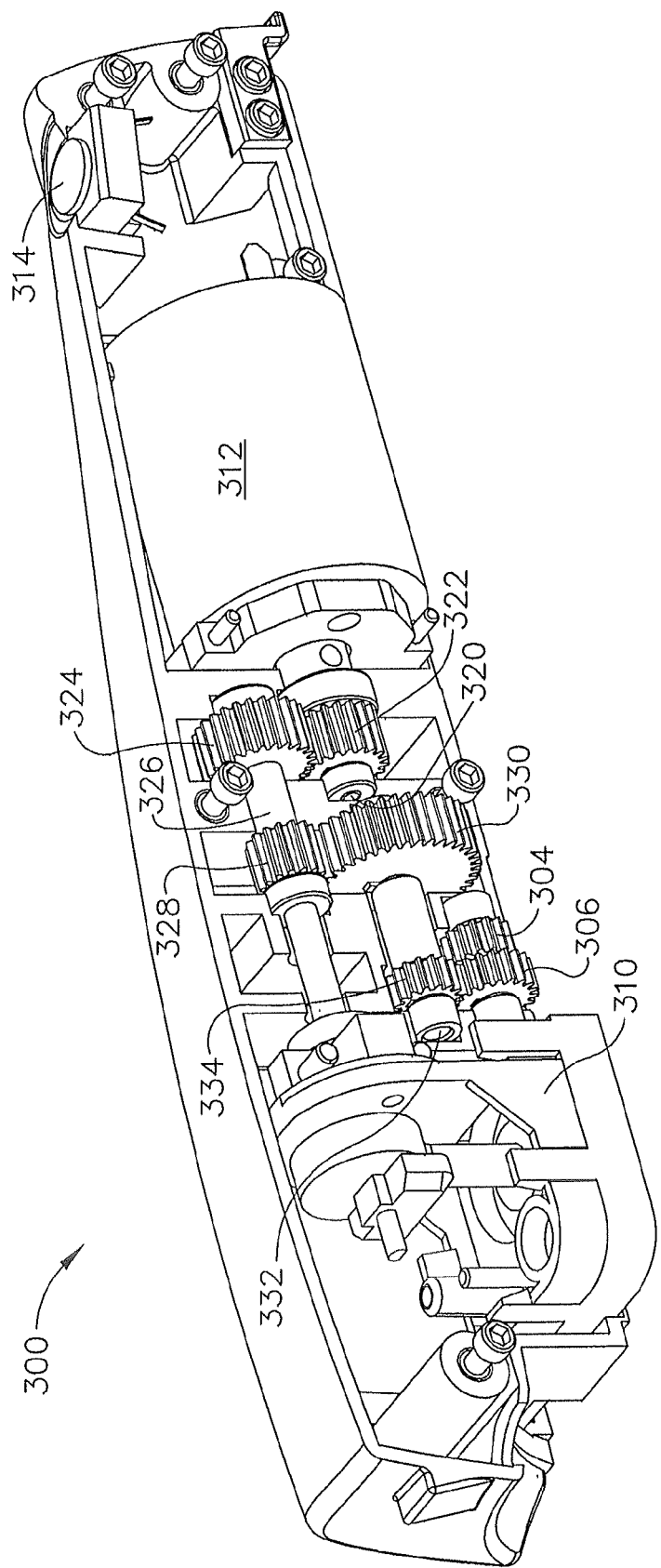
FIG. 4 is a perspective cross-sectional view of the holster of the biopsy device of FIG. 1.
Figure 5:
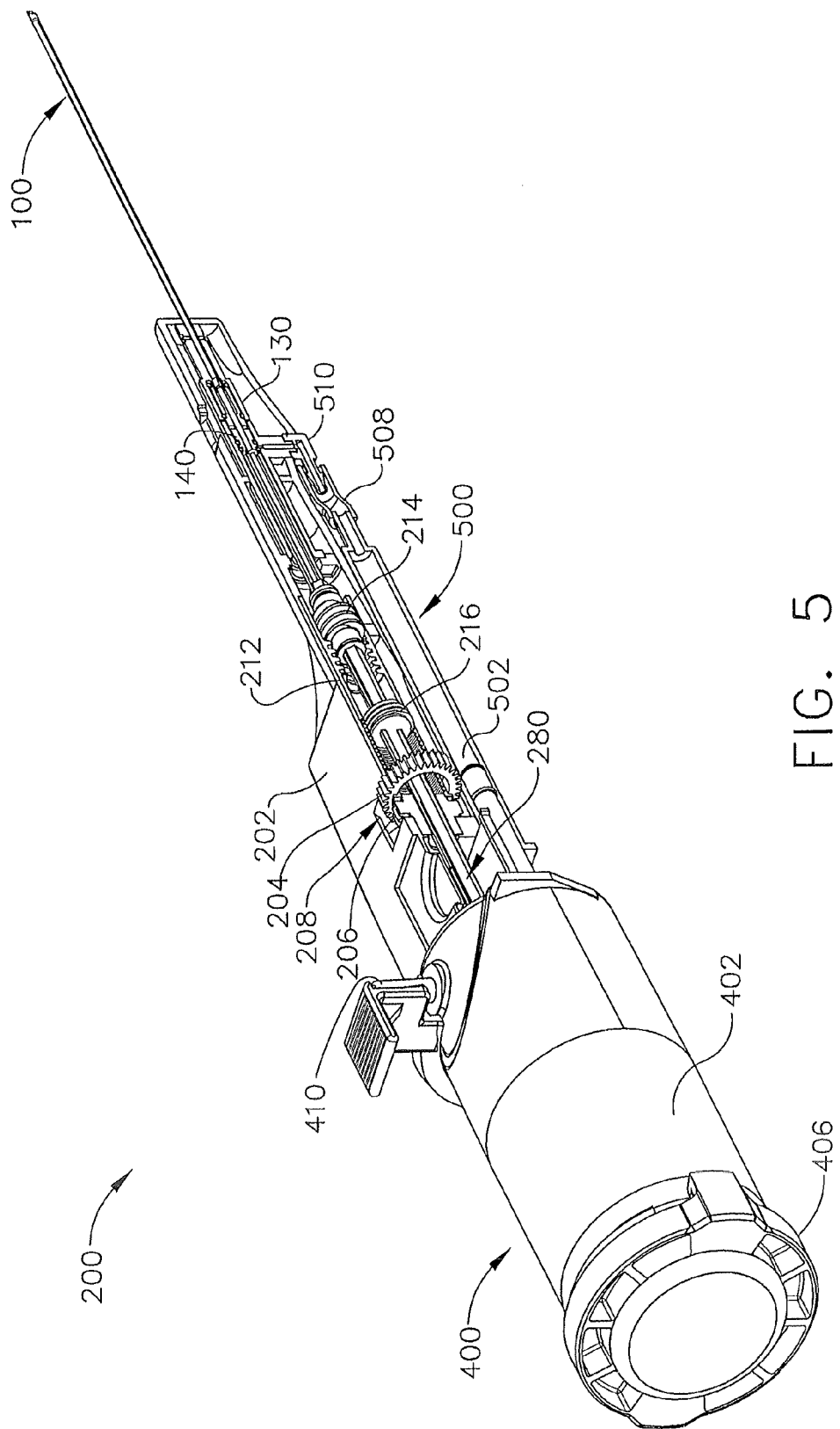
FIG. 5 depicts a perspective view of the probe of the biopsy device of FIG. 1, with all components other than the tissue sample holder being shown in cross-section.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples should not be used to limit the scope of the present invention. Other features, aspects, and advantages of the versions disclosed herein will become apparent to those skilled in the art from the following description, which is by way of illustration, one of the best modes contemplated for carrying out the invention. As will be realized, the versions described herein are capable of other different and obvious aspects, all without departing from the invention. Accordingly, the drawings and descriptions should be regarded as illustrative in nature and not restrictive.

I. Overview

FIGS. 1-18 show an exemplary device (10) that may be used to acquire biopsy samples from a prostate and/or some other location in a patient's anatomy. It should be understood that references herein to procedures involving the prostate are merely illustrative. Device (10) could be used in numerous other locations in a patient's anatomy. The inventor's contemplation is not limited to uses of device (10) in the prostate. There is no intent for device (10) or variations thereof to necessarily be limited to use in a procedure involving a prostate. Device (10) includes a probe (200), a holster (300), a tissue collection chamber (400), and a syringe (500). A needle (100) extends distally from probe (200) and is inserted into a patient's tissue (e.g., prostate, some other location in a patient's anatomy, etc.) to obtain tissue samples as will be described in greater detail below. Holster (300) includes components that are operable to activate a vacuum source and a cutter to assist in capture of the tissue samples. The vacuum pulls the severed tissue sample into tissue collection chamber (400) at the proximal end of probe (200), where the tissue may be retrieved for analysis. Syringe (500) is operable to assist in flushing severed tissue samples into tissue collection chamber (400).

It should be understood that the use of the term "holster" herein should not be read as requiring any portion of probe (200) to be inserted into any portion of holster (300). A variety of types of structures, components, features, etc. (e.g., prongs, bayonet mounts, latches, clamps, clips, snap fittings, etc.) may be used to provide removable coupling of probe (200) and holster (300). Furthermore, in some devices (10), probe (200) and holster (300) may be of unitary or integral construction, such that the two components cannot be separated. By way of example only, in versions where probe (200) and holster (300) are provided as separable components, probe (200) may be provided as a disposable component, while holster (300) may be provided as a reusable component. Still other suitable structural and functional relationships between probe (200) and holster (300) will be apparent to those of ordinary skill in the art in view of the teachings herein.

Device (10) of the present example is sized and configured such that device (10) may be operated by a single hand of a user. In particular, a user may grasp device (10), insert needle (100) into a patient's prostate (or other location in the patient's anatomy), and collect one or a plurality of tissue samples from within the patient's prostate (or other location in the patient's anatomy), all with just using a single hand. Alternatively, a user may grasp device (10) with more than one hand and/or with any desired assistance. It should also be understood that device (10) may be grasped and fully operated by a single hand using a variety of different kinds of grips, including but not limited to a pencil grip. In some settings, the user may capture a plurality of tissue samples with just a single insertion of needle (10) into the patient's prostate (or other location in the patient's anatomy). While examples described herein often refer to the acquisition of biopsy samples from a patient's prostate, and as noted above it should be understood that device (10) may be used in a variety of other procedures for a variety of other purposes and in a variety of other parts of a patient's anatomy (e.g., breast, thyroid, etc.). Various exemplary components, features, configurations, and operabilities of device (10) will be described in greater detail below; while other suitable components, features, configurations, and operabilities will be apparent to those of ordinary skill in the art in view of the teachings herein.

II. Exemplary Probe

As noted above, probe (200) includes a distally extending needle (100). Probe (200) also includes a housing (202), with a pair of gears (204, 206) exposed through an opening (208) in housing (202). A cutter translation gear (204) of probe (200) meshes with exposed gear (304) of holster (300) when probe (200) and holster (300) are coupled together. Similarly, a cutter rotation gear (206) of probe (200) meshes with exposed gear (306) of holster (300) when probe (200) and holster (300) are coupled together. Gears (204, 206, 304, 306) are thereby operable to drive a cutter actuation mechanism to simultaneously rotate and translate a cutter (110) in probe (200) as will be described in greater detail below.

A. Exemplary Needle

Needle (100) is best seen in FIGS. 1-2, 8C, 10C, 12C, 14C, 16C, and 18C. Needle (100) of the present example comprises a cannula (102), piercing tip (104), and a lateral aperture (106) located proximal to tip (104). Cannula (102) of the present example has a size of approximately 18 gauge, though it should be understood that cannula (102) may have any other suitable size. Tissue piercing tip (104) is configured to pierce and penetrate tissue, without requiring a high amount of force, and without requiring an opening to be pre-formed in the tissue prior to insertion of tip (104). Alternatively, tip (104) may be blunt (e.g., rounded, flat, etc.) if desired. Tip (104) may also be configured to provide greater echogenicity than other portions of needle (104), providing enhanced visibility of tip (104) under ultrasound imaging. By way of example only, tip (104) may be configured in accordance with any of the teachings in U.S. Non-Provisional patent application Ser. No. 12/875,200, entitled "Echogenic Needle for Biopsy Device," filed Sep. 3, 2010, the disclosure of which is incorporated by reference herein. Other suitable configurations that may be used for tip (104) will be apparent to those of ordinary skill in the art in view of the teachings herein.

Cannula (102) defines a lumen (108), in which a hollow tubular cutter (110) is slidably disposed. In particular, cutter (110) is operable to rotate and translate within lumen (108), and includes a sharp distal edge (112) that is configured to sever tissue samples protruding through lateral aperture (106), as will be described in greater detail below. Needle (100) also includes a longitudinal wall (120) extending proximally from the proximal portion of tip (104). While wall (120) does not extend along the full length of needle (100) in this example, it should be understood that wall (120) may extend the full length of needle (100) if desired. Wall (120) of the present example proximally terminates at a longitudinal position that is proximal to the longitudinal position of distal cutting edge (112) of cutter (110) when cutter (110) is in a proximal position (see FIG. 10C). Thus, wall (120) and cutter (110) together define a second lumen (122) that is lateral to and parallel to cutter (110). Of course, wall (120) may alternatively proximally terminate at a longitudinal position that is just distal to the longitudinal position of distal cutting edge (112) of cutter (110) when cutter (110) is in a proximal position; or wall (120) may terminate at any other suitable longitudinal position.

Wall (120) includes a plurality of openings (not shown) that provide fluid communication between second lumen (122) and lumen (108) of needle (100), as well as fluid communication between second lumen (122) and the lumen (114) of cutter (110). For instance, as will be described in greater detail below, second lumen (122) may selectively provide atmospheric air to vent cutter lumen (114), or provide saline to flush cutter lumen (114), during operation of device (10) as will be described in greater detail below. The openings in wall (120) are arranged such that at least one opening is located at a longitudinal position that is distal to the distal edge of lateral aperture (106). Thus, cutter lumen (114) and second lumen (122) may remain in fluid communication even when cutter (110) is advanced to a position where cutting edge (112) is located at a longitudinal position that is distal to the longitudinal position of the distal edge of lateral aperture (106) (see FIG. 8C). Of course, as with any other component described herein, any other suitable configurations may be used. For instance, wall (120) may simply be omitted in some versions, such that only cutter (110) and the inner surface of needle (100) define second lumen (122). In some such versions, second lumen (122) remains in fluid communication with cutter lumen (114) even when cutter (110) is at a distal-most position.

As best seen in FIGS. 3, 5, 8C, 10C, 12C, 14C, 16C, and 18C, probe (200) of the present example also includes a manifold (130) that is secured to the proximal end of cannula (102) via a set screw (not shown) disposed in opening (131). Of course, manifold (130) may alternatively be secured relative to cannula (102) in any other suitable fashion (e.g., overmolding, etc.). In some versions, opening (131) provides a port for an adhesive. Manifold (130) defines a hollow interior (132) that is in fluid communication with second lumen (122). Manifold (130) further includes a first set of openings (134) in fluid communication with hollow interior (132) and a second opening (136) in fluid communication with hollow interior (132). First set of openings (134) is in fluid communication with atmospheric air, thereby providing a vent. Second opening (136) is in fluid communication with syringe (500), as will be described in greater detail below. A shuttle valve slider (140) translates within hollow interior (132) to selectively couple either first set of openings (134) or second opening (136) with second lumen (122), while sealing the other of openings (134) or opening (136) relative to second lumen (122), based on the longitudinal position of cutter (110) as will be described in greater detail below.

It should be understood that, as with other components described herein, needle (100) may be varied, modified, substituted, or supplemented in a variety of ways; and that needle (100) may have a variety of alternative features, components, configurations, and functionalities. A plurality of external openings (not shown) may also be formed in needle (100), and may be in fluid communication with a lumen of needle (100) that is lateral to cutter (110). For instance, such external openings may be configured in accordance with the teachings of U.S. Pub. No. 2007/0032742, entitled "Biopsy Device with Vacuum Assisted Bleeding Control," published Feb. 8, 2007, the disclosure of which is incorporated by reference herein. Cutter (110) may also include one or more side openings (not shown). Of course, as with other components described herein, such external openings in needle (100) and cutter (110) are merely optional. As yet another merely illustrative example, needle (100) may be constructed in accordance with the teachings of U.S. Pub. No. 2008/0214955, the disclosure of which is incorporated by reference herein, and/or in accordance with the teachings of any other reference cited herein. As another merely illustrative example, needle (100) may simply lack second lumen (122) altogether in some versions. Still other suitable ways in which needle (100) may be configured will be apparent to those of ordinary skill in the art in view of the teachings herein.

B. Exemplary Cutter Actuation Mechanism

Figure 6:
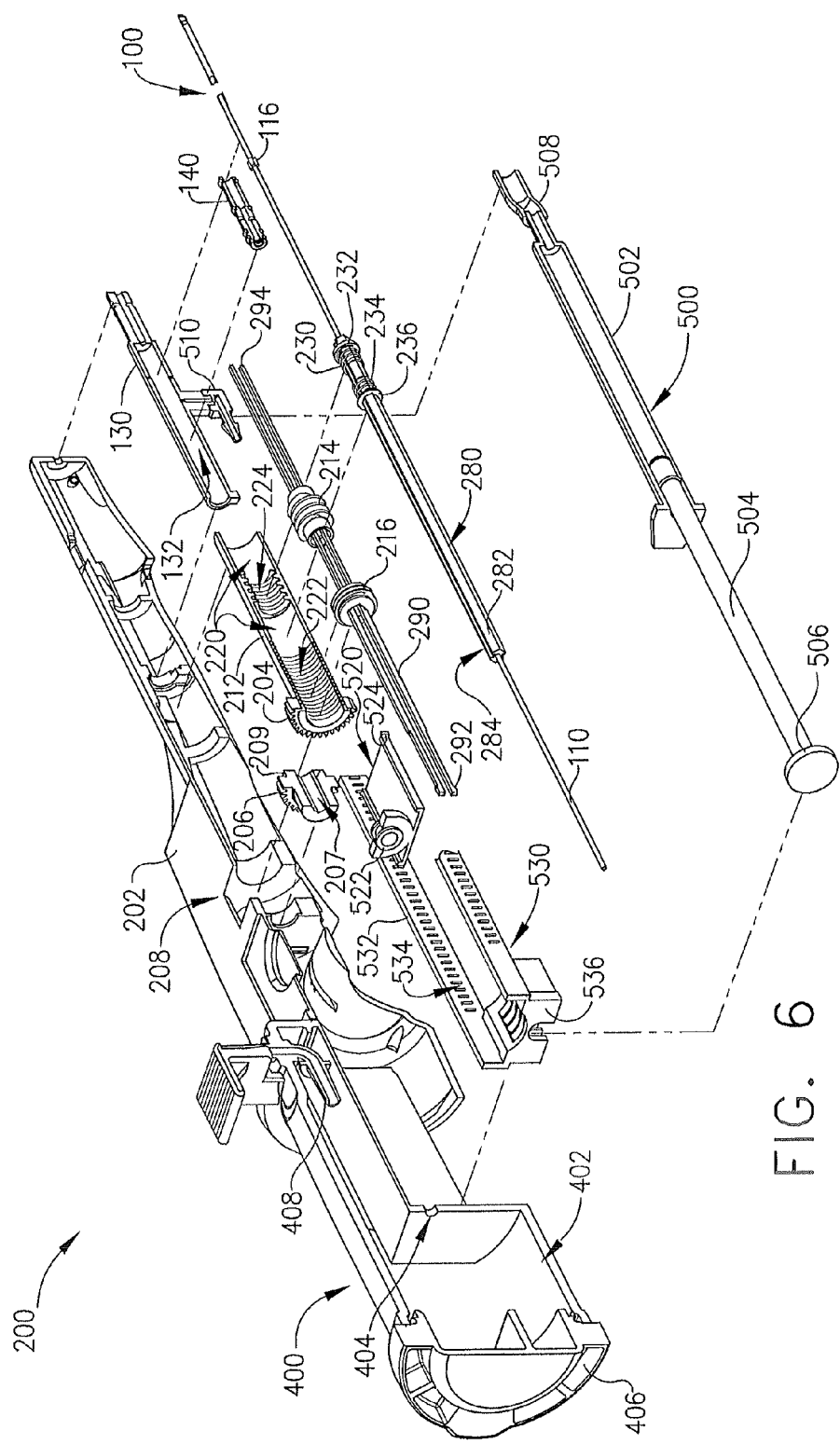
FIG. 6 depicts an exploded perspective view of the probe of FIG. 5, with several of the parts being shown in cross-section.

As noted above, probe (200) of the present example includes components that are operable to simultaneously rotate and translate cutter (110) within needle (100) to sever biopsy samples from tissue protruding through lateral aperture (106). In particular, and as best seen in FIGS. 6, 8C, 10C, 12C, 14C, 16C, and 18C, probe (200) includes a drive nut (212), a cutter lead screw (214), translation gear (204), rotation gear (206), and a cutter overmold (280). Cutter overmold (280) is secured unitarily to the exterior of the proximal portion of cutter (110). In particular, cutter overmold (280) is formed of plastic that is overmolded about metal cutter (110). Of course, cutter overmold (280) may be formed of any other suitable material or combination of materials and/or may be secured to cutter (110) using any other suitable technique or combination of techniques. With cutter overmold (280) being secured unitarily to cutter (110) in the present example, cutter overmold (280) and cutter (110) rotate and translate unitarily. As will be described in greater detail below, such rotation and translation is provided by simultaneous rotation of translation gear (204) and rotation gear (206). As best seen in FIG. 6, cutter overmold (280) includes a set of exterior flats (282). An opposing pair of recesses (284) extend longitudinally along exterior flats (282). Of course, this configuration of cutter overmold (280) is merely one example. Various other suitable configurations for cutter overmold (280) will be apparent to those of ordinary skill in the art in view of the teachings herein.

Rotation gear (206) is positioned about exterior flats (282). Rotation gear (206) includes a plurality of interior flats (207) that complement exterior flats (282). Thus, rotation gear (206) rotates unitarily with cutter overmold (280). Accordingly, with cutter overmold (280) being unitary with cutter (110), rotation of rotation gear (206) drives rotation of cutter (110) in the present example. While rotation gear (206) rotates unitarily with cutter overmold (280) in the present example, rotation gear (206) is not fixed to cutter overmold (280). Thus, cutter overmold (280) is permitted to translate relative to rotation gear (206). It should be understood that cutter overmold (280) and rotation gear (206) may include a variety of other features (e.g., in lieu of complementary flats (207, 282)) to provide rotation of cutter (110) by rotation of rotation gear (206), including but not limited to complementary teeth or splines, a complementary key and keyway, etc. It should also be understood that cutter (110) and rotation gear (206) may be in communication via a variety of alternative intermediary components, including but not limited to one or more gears or elongate members with splines.

Cutter lead screw (214) is also positioned about flats (282). In particular, cutter lead screw (214) includes a plurality of interior flats (not shown) that complement flats (282). Thus, cutter lead screw (214) rotates unitarily with cutter overmold (280) (and, hence, cutter (110)) in the present example. In addition, cutter lead screw (214) is slidably disposed about flats (282). A distal coil spring (230) is positioned about cutter overmold (280), distal to cutter lead screw (214). An "e-clip" (232) is secured to cutter overmold (280), distal to distal coil spring (230), such that distal coil spring (230) is longitudinally positioned between cutter lead screw (214) and e-clip (232). Thus, e-clip (232) and distal coil spring (230) cooperate to resiliently bias cutter lead screw (214) proximally. A proximal coil spring (234) is also positioned about cutter overmold (280), proximal to cutter lead screw (214). Another e-clip (236) is secured to cutter overmold (280), proximal to proximal coil spring (234), such that proximal coil spring (234) is longitudinally positioned between cutter lead screw (214) and e-clip (236). Thus, e-clip (236) and proximal coil spring (234) cooperate to resiliently bias cutter lead screw (214) distally. In other words, springs (230, 234) opposingly resiliently bias cutter lead screw (214) to urge cutter lead screw (214) to a longitudinal position that is substantially centered between e-clips (232, 236).

In some other versions, cutter lead screw (214) is secured unitarily to cutter overmold (280), such that cutter lead screw (214) translates unitarily with cutter overmold (280) (and, hence, cutter (110)). In some such versions, distal coil spring (230) is still positioned about cutter overmold (280), to bias cutter lead screw (214) proximally when cutter lead screw (214) reaches a distal free-wheeling region (220) of drive nut (212) as described below. Of course, cutter lead screw (214) and the distal portion of cutter overmold (280) may have any other suitable features, configurations, and relationships.

Translation gear (204) is integrally formed at the proximal end of drive nut (212) in the present example. For instance, translation gear (204) and drive nut (212) may be molded as a single unitary component. Alternatively, any other suitable techniques may be used to form and/or join translation gear (204) and drive nut (212). Rotation gear (206) includes a hub portion (209) that fits within part of the interior of translation gear (204), providing support to translation gear (204) and drive nut (212). Rotation gear (206) is nevertheless rotatable relative to translation gear (204). In the present example, drive nut (212) rotates unitarily with translation gear (204), yet drive nut (212) does not translate relative to housing (202). Drive nut (212) is in communication with cutter lead screw (214) and plunger lead screw (216) via interior threads along a portion of its length. In particular, drive nut (212) of the present example includes fine pitch region (222) near its proximal end and coarse pitch region (224) near its distal end. Drive nut (212) also includes a non-threaded free-wheeling region (220) distal of coarse pitch region (224) and a non-threaded free-wheeling region (220) proximal to coarse pitch region (224).

Cutter lead screw (214) includes external threading that has a relatively coarse pitch and that complements the internal threading of the coarse pitch region (224) of drive nut (212). Cutter lead screw (214) is positioned along the coarse pitch region (224) of drive nut (212) during a range of longitudinal travel of cutter lead screw (214), such that the threads of cutter lead screw (214) engage with the threads of coarse pitch region (224) of drive nut (212). As noted above, cutter lead screw (214) is further associated with cutter (110). With such a configuration, and as will also be described in greater detail below, rotation of cutter lead screw (214) relative to drive nut (212) causes cutter lead screw (214) and cutter (110) to translate longitudinally.

Figure 9:
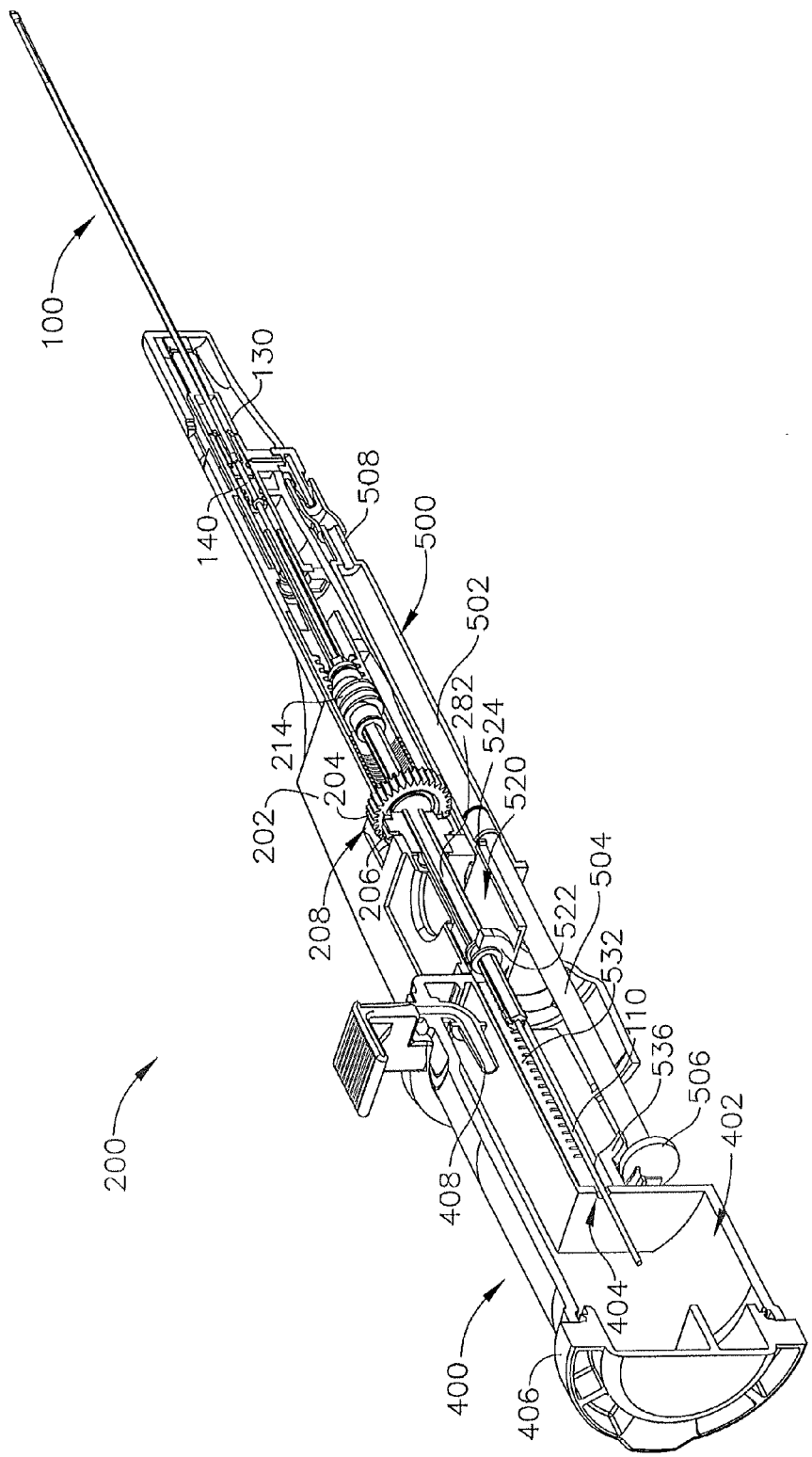
FIG. 9 depicts a perspective cross-sectional view of the probe of FIG. 5, with the probe being configured at a stage of use where the cutter is retracted to open the lateral aperture of the needle.

When cutter lead screw (214) translates to a distal-most position (as shown in FIGS. 13-18), cutter lead screw (214) encounters the distal free-wheeling region (220) of drive nut (212). When cutter lead screw (214) encounters the distal free-wheeling region (220), cutter (110) is at a distal position, and cutter lead screw (214) (and, hence, cutter (110)) ceases further distal translation despite continued rotation of cutter lead screw (214) relative to drive nut (212). However, once the direction of rotation of cutter lead screw (214) and drive nut (212) is reversed at this stage, distal coil spring (230) urges cutter lead screw (214) back into engagement with coarse pitch region (224), which in turn provides proximal translation of cutter lead screw (214) and cutter (110). After sufficient proximal translation, when cutter lead screw (214) translates to a proximal-most position (as shown in FIGS. 9-10), cutter lead screw (214) encounters the proximal free-wheeling region (220) of drive nut (212). When cutter lead screw (214) encounters the proximal free-wheeling region (220), cutter (110) is at a proximal position, and cutter lead screw (214) (and, hence, cutter (110)) ceases further proximal translation despite continued rotation of cutter lead screw (214) relative to drive nut (212). When the direction of rotation of cutter lead screw (214) and drive nut (212) is reversed yet again, proximal coil spring (234) urges cutter lead screw (214) back into engagement with coarse pitch region (224), providing distal translation of cutter lead screw (214) and cutter (110).

In the present example, and as noted above, gears (204, 206) are rotated simultaneously during operation of device (10). In particular, gears (204, 206) are rotated simultaneously in the same direction in the present example. Thus, cutter overmold (280), cutter lead screw (214), and drive nut (212) all rotate simultaneously and in the same direction during operation of device (10). However, gears (204, 206) have different pitch diameters in the present example, such that gears (204, 206) will rotate simultaneously at different speeds. Accordingly, in the present example, cutter overmold (280) and cutter lead screw (214) will all rotate based on one rotational speed; while drive nut (212) will simultaneously rotate at a different rotational speed. So even though cutter lead screw (214) and drive nut (212) rotate simultaneously in the same direction, the difference between rotational speeds of cutter lead screw (214) and drive nut (212) provide a net result of cutter lead screw (214) rotating relative to drive nut (212). Due to interaction between threading of cutter lead screw (214) and threading of coarse pitch region (222) in drive nut (212), such relative rotation provides translation of cutter (110) while cutter (110) rotates as described above.

In some other versions, drive nut (212) simply stays stationary relative to housing (202) and does not rotate at all. In such versions, rotation of cutter lead screw (214) is still relative to drive nut (212), which will still provide translation of cutter (110). It should therefore be understood that translation gear (204) is merely optional. In some other versions, rotation gear (206) is rotated in a direction opposite to the direction of rotation of translation gear (204). It should also be understood that there are a variety of other ways to associate drive nut (212), cutter lead screw (214), cutter (110), translation gear (204), and rotation gear (206) to achieve translation and rotation of cutter (110). Other suitable components, features, variations, operabilities, and relationships between these components will be apparent to those of ordinary skill in the art in view of the teachings herein.

Figure 7:
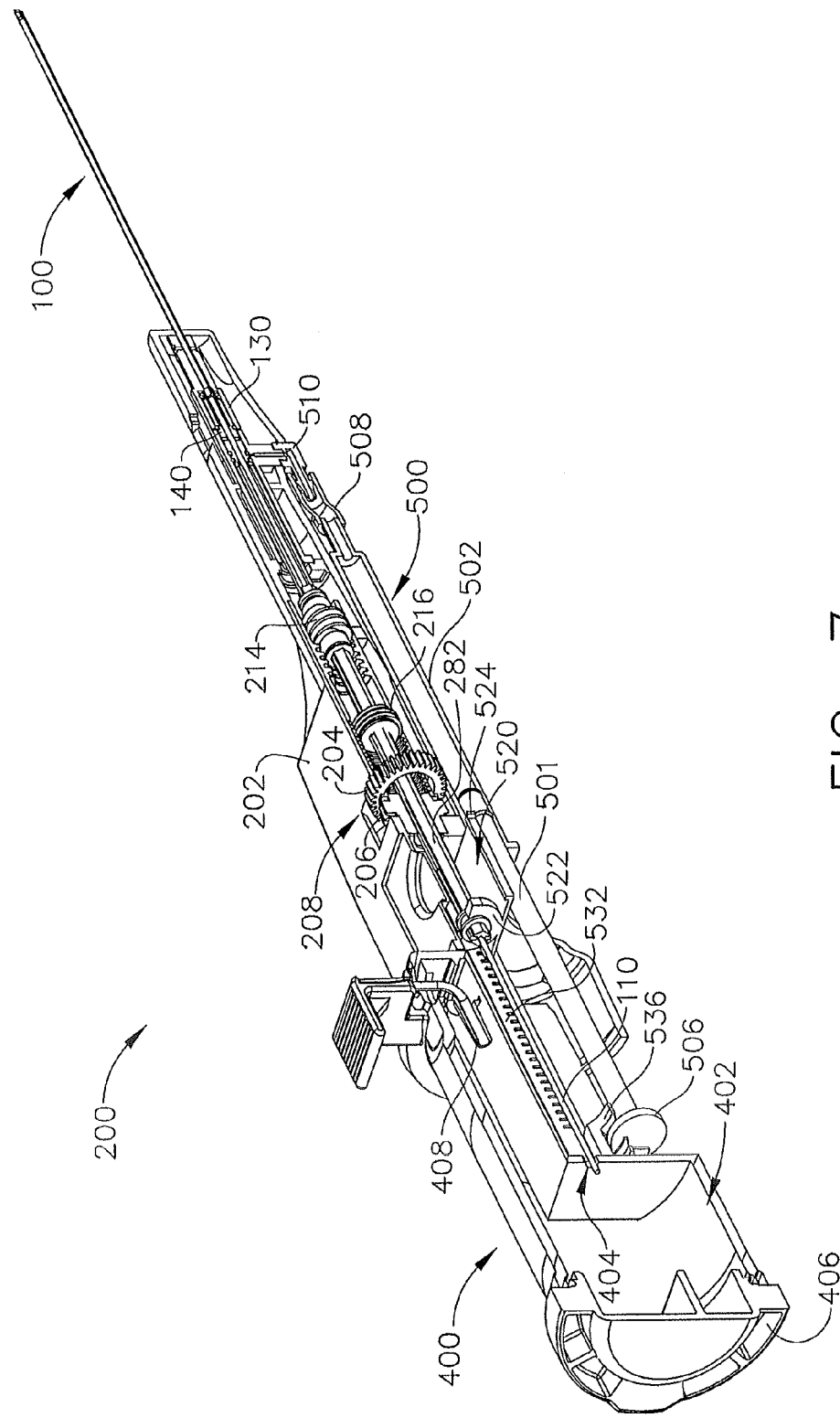
FIG. 7 depicts a perspective cross-sectional view of the probe of FIG. 5, with the probe being configured at a stage of use where the probe is ready for insertion in a patient.
Figure 8A:
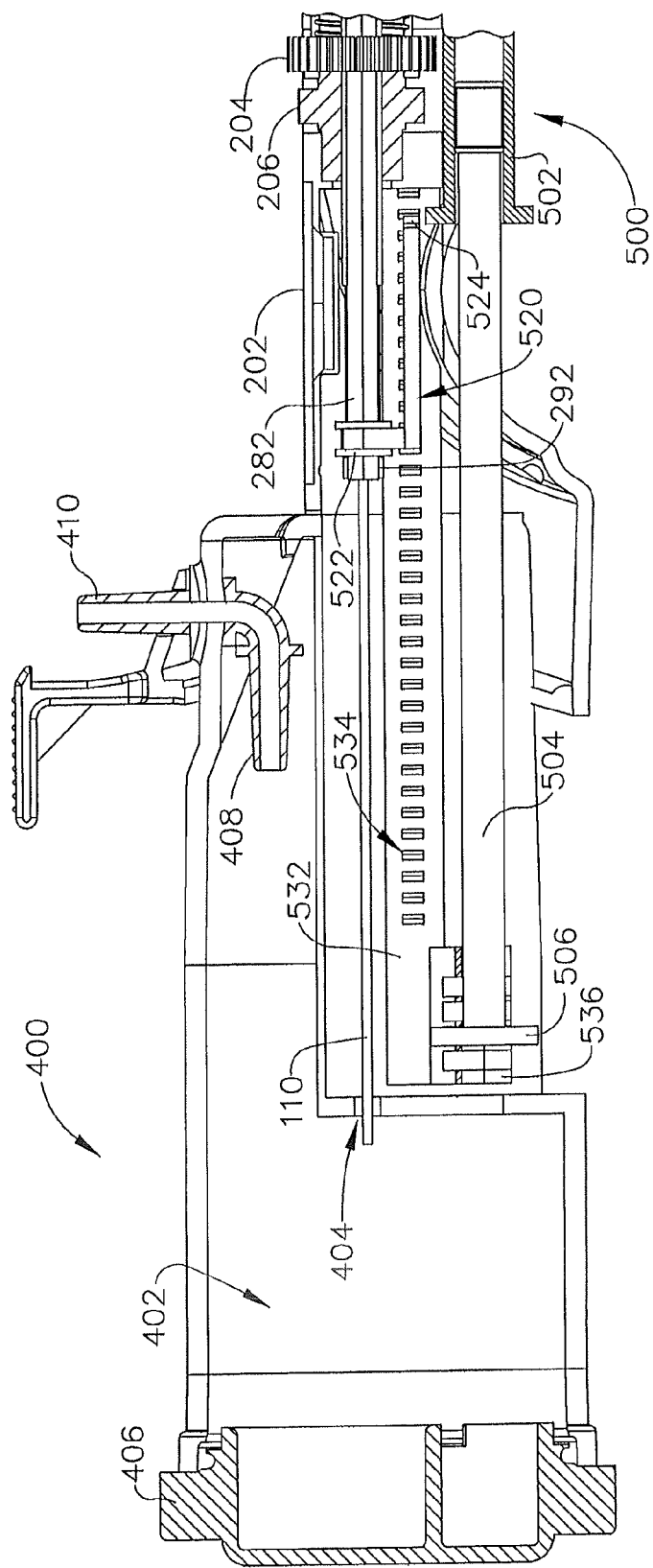
FIG. 8A depicts a partial cross-sectional view of a proximal region of the probe in FIG. 5, in the stage of use of FIG. 7.
Figure 8B:
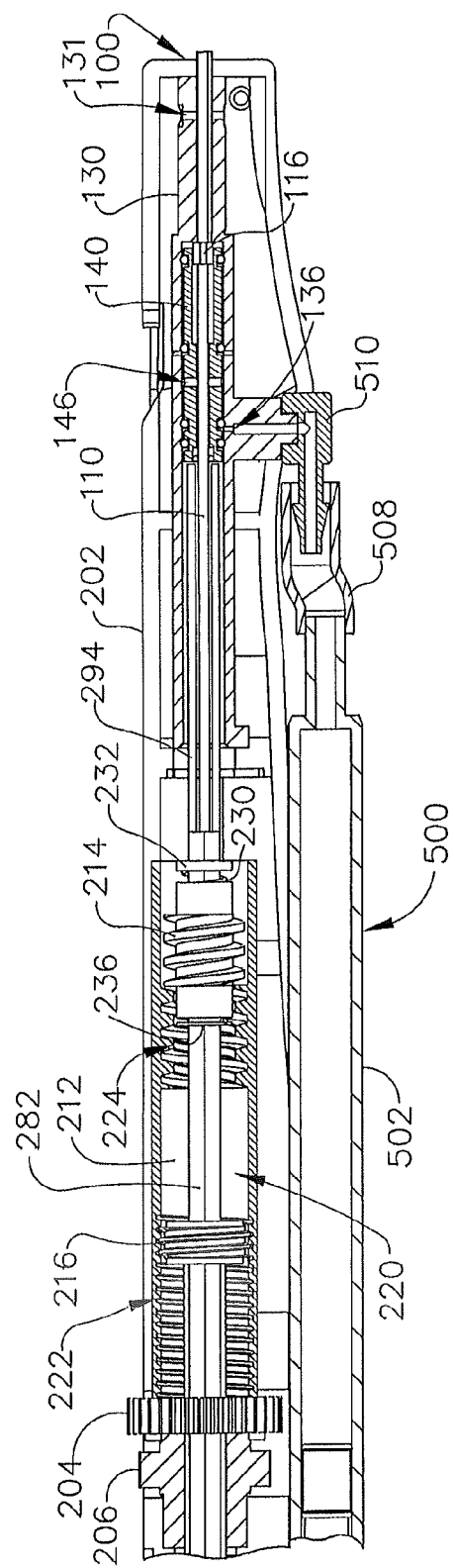
FIG. 8B depicts partial cross-sectional view of an intermediate region of the probe in FIG. 5, in the stage of use of FIG. 7.

An example of operation of the above-described cutter actuation components is shown in FIGS. 7-16. In FIGS. 7-8, cutter (110) starts at a distal position, effectively closing lateral aperture (106). As shown in FIG. 8B, cutter lead screw (214) is in the distal free-wheeling region (220) at this stage, with distal spring (230) biasing cutter lead screw (214) proximally toward coarse pitch region (224). Gears (204, 206) are then rotated to retract cutter (110) proximally. Cutter (110) eventually reaches the proximal position shown in FIGS. 9-10, with cutter lead screw (214) traversing coarse pitch region (224) along the way. As shown in FIG. 10B, cutter lead screw (214) is in the proximal free-wheeling region (220) at this stage, with proximal spring (234) biasing cutter lead screw (214) distally toward coarse pitch region (224). It should be understood that, during the transition from the stage shown in FIGS. 7-8 to the stage shown in FIGS. 9-10, cutter lead screw (214) may substantially compress proximal spring (234) such that cutter lead screw (214) pushes cutter (110) proximally by impinging against proximal e-clip (236). It should also be understood that cutter (110) rotates during the transition from the stage shown in FIGS. 7-8 to the stage shown in FIGS. 9-10.

Figure 10A:
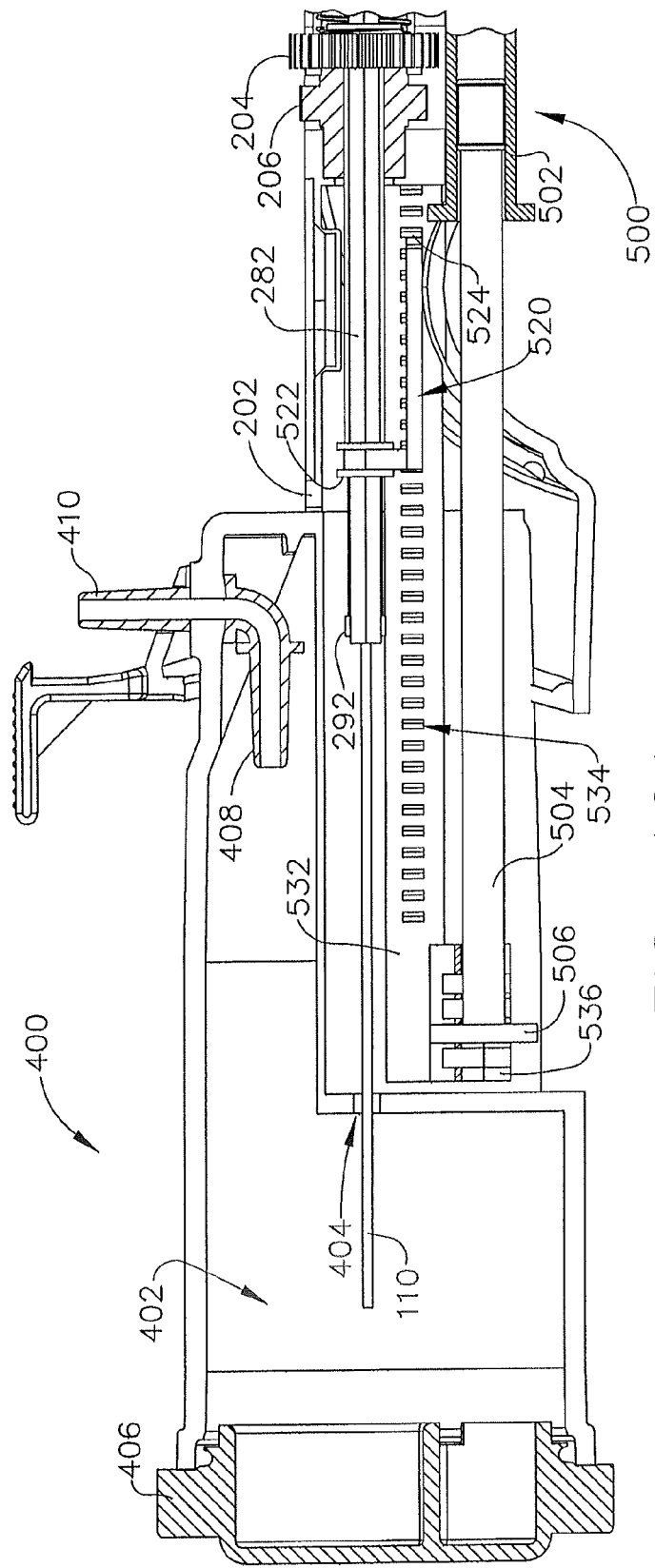
FIG. 10A depicts a partial cross-sectional view of a proximal region of the probe in FIG. 5, in the stage of use of FIG. 9.
Figure 10B:
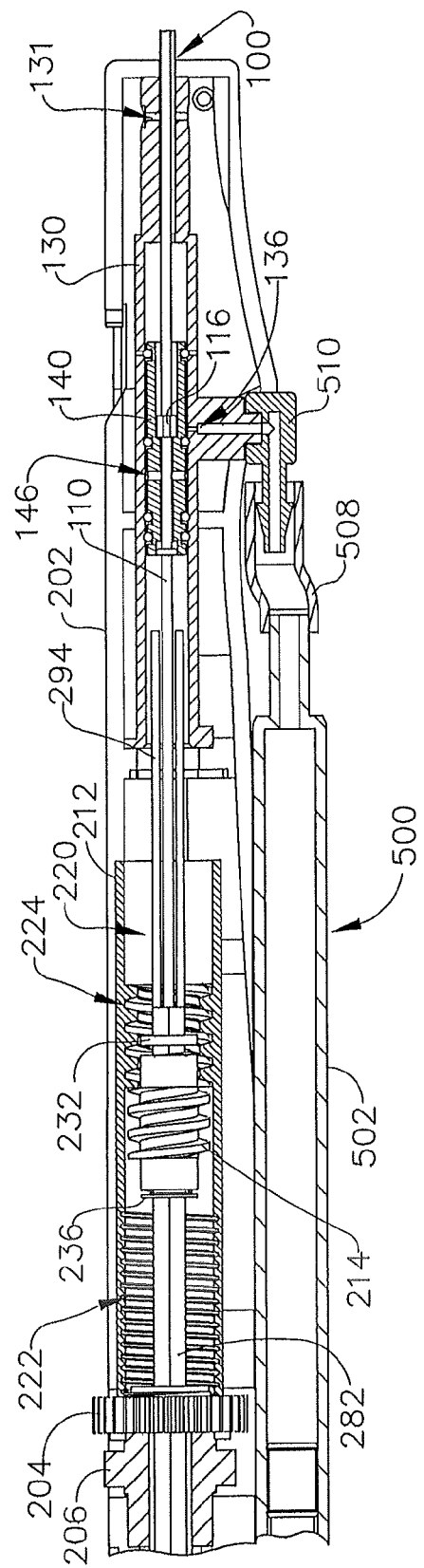
FIG. 10B depicts partial cross-sectional view of an intermediate region of the probe in FIG. 5, in the stage of use of FIG. 9.
Figure 11:
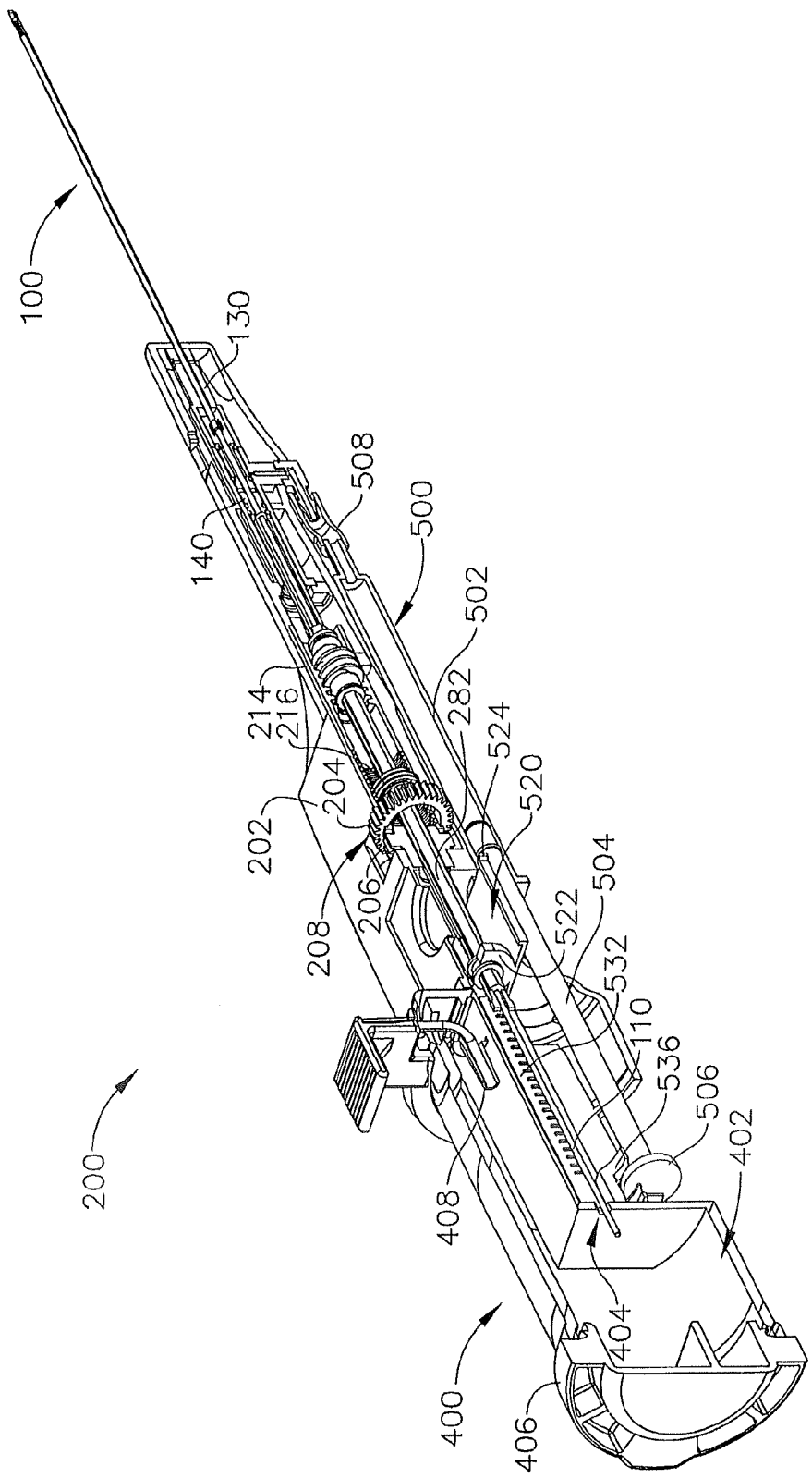
FIG. 11 depicts a perspective cross-sectional view of the probe of FIG. 5, with the probe being configured at a stage of use where the cutter is partially actuated to sever a tissue sample.
Figure 12A:
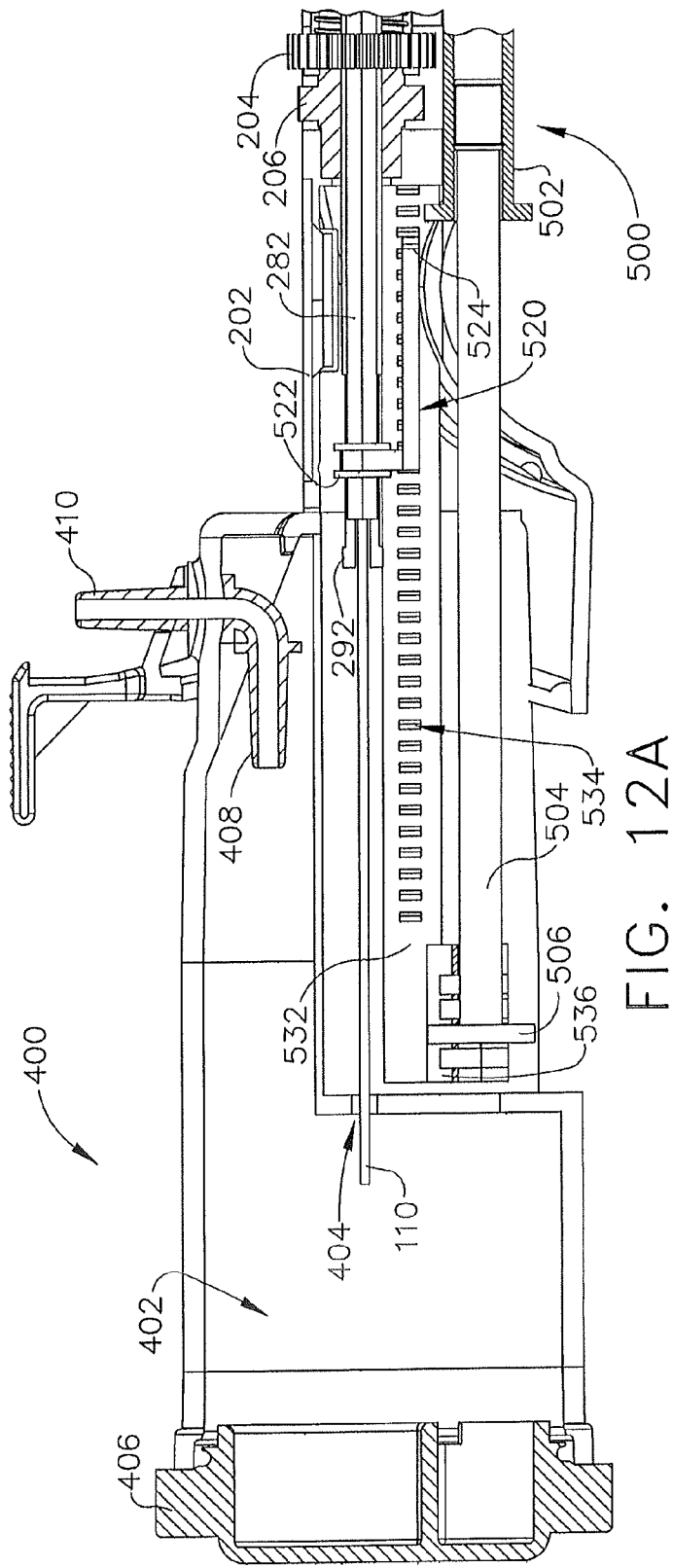
FIG. 12A depicts a partial cross-sectional view of a proximal region of the probe in FIG. 5, in the stage of use of FIG. 11.
Figure 12B:
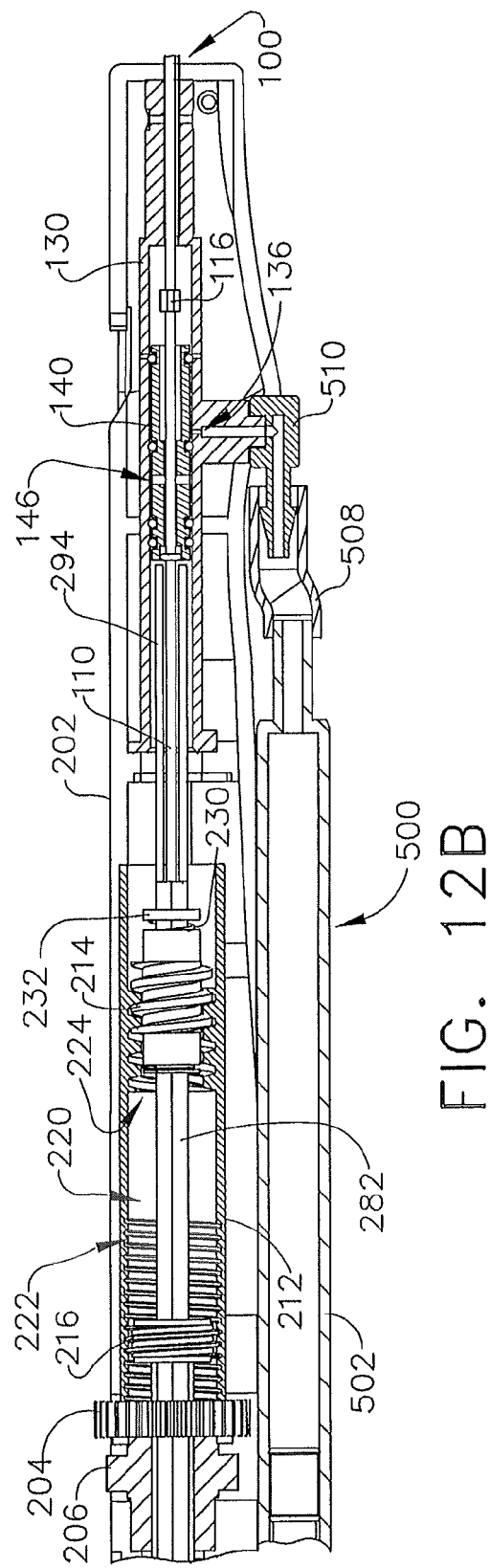
FIG. 12B depicts partial cross-sectional view of an intermediate region of the probe in FIG. 5, in the stage of use of FIG. 11.

With tissue drawn in lateral aperture (106) as described elsewhere herein, the rotational direction of gears (204, 206) is reversed to advance cutter (110) distally to sever a biopsy sample from tissue protruding in lateral aperture (106). FIGS. 11-12 depict an intermediate stage of such distal advancement of cutter (110). As shown in FIG. 12B, cutter lead screw (214) is in coarse pitch region (224) at this stage. It should be understood that, during the transition from the stage shown in FIGS. 9-10 to the stage shown in FIGS. 11-12, cutter lead screw (214) may substantially compress distal spring (230) such that cutter lead screw (214) pushes cutter (110) distally by impinging against distal e-clip (232). It should also be understood that cutter (110) rotates during the transition from the stage shown in FIGS. 9-10 to the stage shown in FIGS. 11-12. Cutter (110) eventually reaches the position shown in FIGS. 13-14, where cutter (110) has completed severing a biopsy sample (not shown) from tissue protruding in lateral aperture (106). As shown in FIG. 14B, cutter lead screw (214) is in the distal free-wheeling region (220) again at this stage, with distal spring (230) biasing cutter lead screw (214) proximally toward coarse pitch region (224). The above process may be repeated as many times as desired until a satisfactory number of tissue samples have been captured.

By way of example only, the cutter actuation mechanism of device (10) may be constructed in accordance with the teachings of U.S. Pub. No. 2010/0317997. As another merely illustrative example, the cutter actuation mechanism may be constructed in accordance with the teachings of U.S. Pub. No. 2008/0214955. As yet another merely illustrative example, the cutter actuation mechanism may be constructed in accordance with the teachings of U.S. Pub. No. 2010/0292607, entitled "Tetherless Biopsy Device with Self-Reversing Cutter Drive Mechanism," published Nov. 18, 2010, the disclosure of which is incorporated by reference herein. Alternatively, the cutter actuation mechanism may be constructed in accordance with the teachings of any other reference cited herein. It should also be understood that device (10) may be configured such that cutter (110) does not translate (e.g., such that cutter (110) merely rotates, etc.); or such that cutter (110) does not rotate (e.g., such that cutter (110) merely translates, etc.). As another merely illustrative example, cutter (110) may be actuated pneumatically in addition to or in lieu of being actuated by mechanical components. Other suitable alternative versions, features, components, configurations, and functionalities of a cutter actuation mechanism will be apparent to those of ordinary skill in the art in view of the teachings herein.

C. Exemplary Syringe Actuation Mechanism

Probe (200) of the present example includes components that are operable to actuate syringe (500) and also drive shuttle valve slider (140) in manifold (130), thereby controlling fluid communication to second lumen (122) of needle (100). In particular, and as best seen in FIGS. 6-18, probe (200) includes a plunger lead screw (216), a ratcheting member (520), and an actuation frame (530). Like cutter lead screw (214) as described above, plunger lead screw (216) is driven by simultaneous rotation of translation gear (204) and rotation gear (206). Plunger lead screw (216) is also positioned about exterior flats (282) and has interior flats (not shown) complementing exterior flats (282), such that plunger lead screw (216) rotates unitarily with cutter overmold (280).

Plunger lead screw (216) includes exterior threading having a relatively fine pitch. This exterior threading complements the threading in a fine pitch region (222) in the interior of drive nut (212). Plunger lead screw (216) is longitudinally positioned within fine pitch region (222) during operation of device (10). Thus, as plunger lead screw (216) rotates relative to drive nut (212) (or vice versa), the interaction between the complementary threading provides translation of plunger lead screw. Such relative rotation is provided through plunger lead screw (216) and drive nut (212) rotating simultaneously in the same direction at different speeds, such that plunger lead screw (216) is driven longitudinally in a manner very similar to that described above with respect to cutter lead screw (214). In particular, since gear (204) rotates at a speed that is different from the speed at which gear (206) rotates, since drive nut (212) rotates at the same speed as gear (204), and since plunger lead screw (216) rotates at the same speed as gear (206), drive nut (212) and plunger lead screw (216) rotate at different speeds. So even though drive nut (212) and plunger lead screw (216) rotate simultaneously and in the same direction, the net result is that plunger lead screw (216) rotates relative to drive nut (212).

As best seen in FIG. 6, a pair of arms (290) extend proximally and distally from plunger lead screw (216). In the present example, arms (290) are unitarily secured to plunger lead screw (216), such that arms (290) rotate and translate unitarily with plunger lead screw (216). For instance, plunger lead screw (216) and arms (290) may be molded together as a single piece. Alternatively, plunger lead screw (216) and arms (290) may be formed in any other suitable fashion. Arms (290) are received in longitudinal recesses (284) of cutter overmold (280) in the present example. Recesses (284) are deep enough to accommodate arms (290) such that arms (290) do not protrude radially outwardly from cutter overmold (280). With arms (290) being received in longitudinal recesses (284), arms (290) and plunger lead screw (216) rotate unitarily with cutter overmold (280). However, neither arms (290) nor plunger lead screw (216) are fixed to cutter overmold (280). Thus, arms (290) and plunger lead screw (216) are allowed to translate relative to cutter overmold (280). Plunger lead screw (216) and arms (290) are also permitted to translate relative to rotation gear (206) in the present example. In particular, longitudinal recesses (284) and arms (290) are dimensioned such that the combination of arms (290) and cutter overmold (280) are permitted to translate relative to and within rotation gear (206).

Arms (290) include a proximal latching feature (292) that couples with a ratcheting member (520). In particular, ratcheting member (520) includes a yoke (522) that receives latching feature (292). The engagement between yoke (522) and latching feature (292) provides translation of ratcheting member (520) in response to translation of arms (290) and plunger lead screw (216), as will be described in greater detail below. Ratcheting member (520) includes a pair of outwardly extending tabs (524), which are received in slots (534) formed in arms (532) of an actuation frame (530). Tabs (524) are configured such that ratcheting member (520) pulls actuation frame (530) distally when ratcheting member (520) is pulled distally by arms (290) and plunger lead screw (216). However, tabs (524) are further configured such that tabs (524) ratchet against arms (532) when ratcheting member (520) is pushed proximally by arms (290) and plunger lead screw (216), such that tabs (524) move proximally into engagement with a respective proximal pair of slots (534) while actuation frame (530) remains substantially stationary. Thus, as ratcheting member (520) is reciprocated proximally and distally, ratcheting member (520) pulls actuation frame (530) distally in an incremental fashion during distal movement of ratcheting member (520); while not moving actuation frame (530) during proximal movement of ratcheting member (520).

Actuation frame (530) includes a plunger holder (536) that is coupled with syringe (500). Syringe (500) of this example is a conventional syringe, and includes a barrel (502), a plunger (504), and a pusher (506) at the proximal end of plunger (504). Barrel (502) contains saline in the present example, though it should be understood that any other suitable fluid may be used. Syringe (500) expels the saline distally from barrel (502) when plunger (504) is advanced distally. Plunger holder (536) is coupled with pusher (506), such that each time actuation frame (530) is advanced distally, plunger (504) is pushed distally, thereby expelling saline distally from barrel (502). A conduit (508) couples barrel (502) with a coupling (510), which is in fluid communication with second opening (136) of manifold (130). Thus, as plunger holder (536) and plunger (504) are advanced distally by actuation frame (530), arms (290) and plunger lead screw (216), saline is communicated from barrel (502) to second opening (136) of manifold (130). This fluid communication to manifold (130) is further complemented by actuation of shuttle valve slider (140) by distal ends (294) of arms (290) as will be described in greater detail below.

Figure 13:
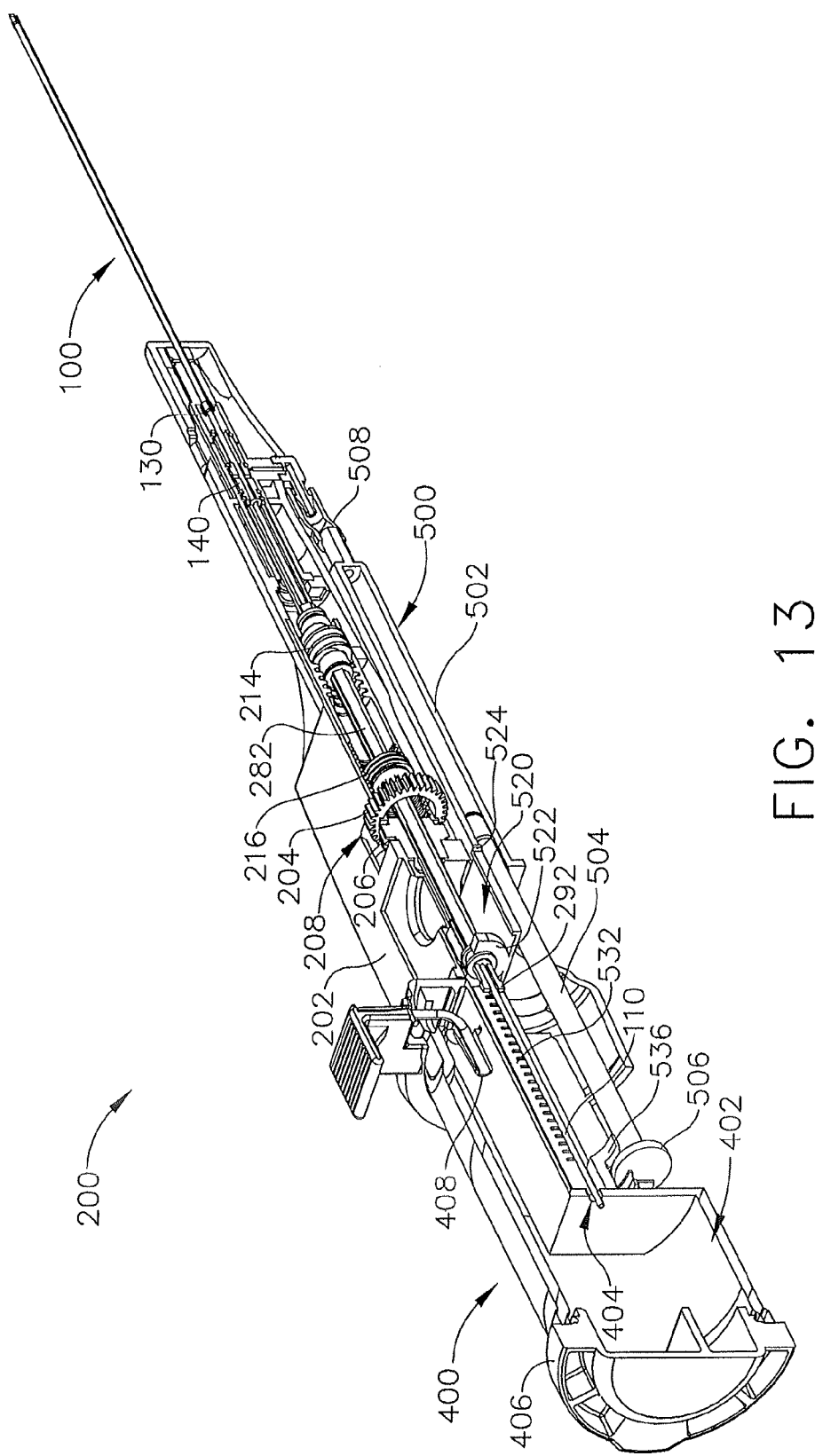
FIG. 13 depicts a perspective cross-sectional view of the probe of FIG. 5, with the probe being configured at a stage of use where the cutter is fully actuated and the valve assembly is partially actuated.
Figure 14A:
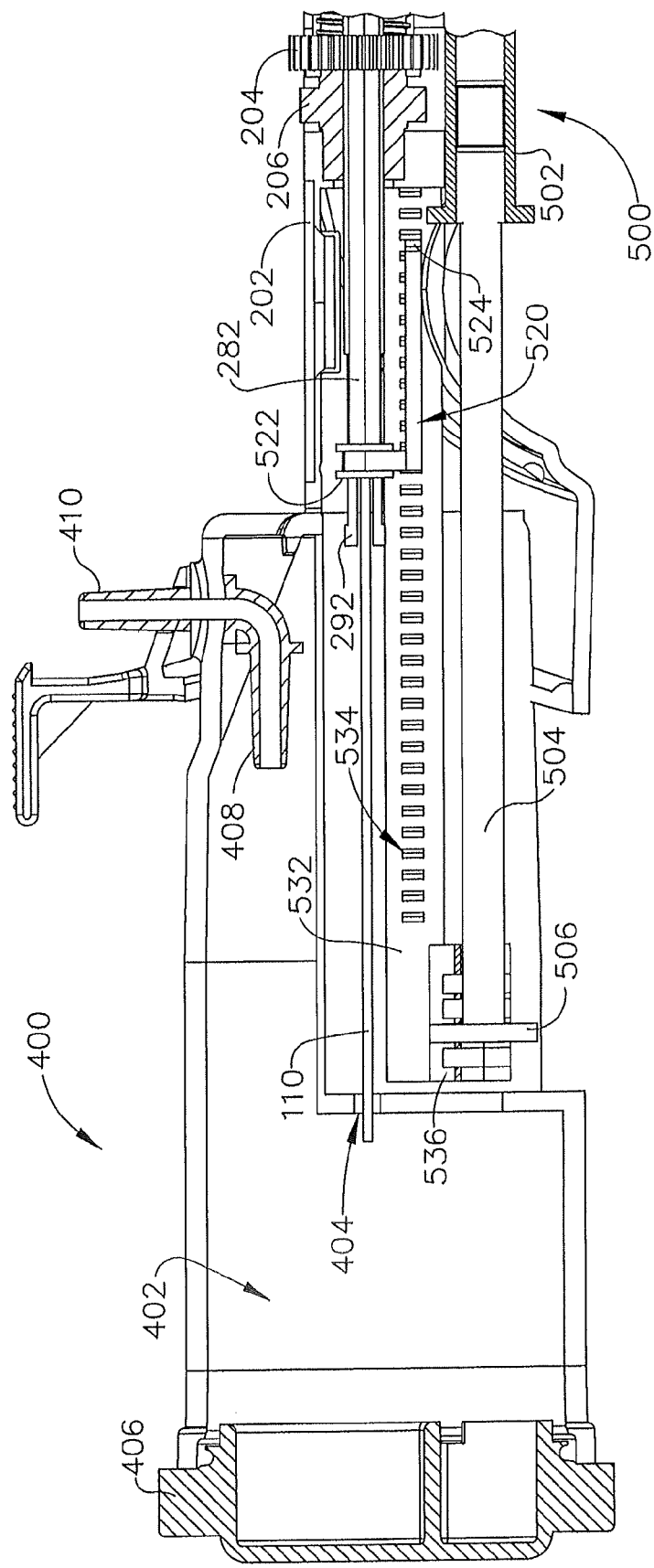
FIG. 14A depicts a partial cross-sectional view of a proximal region of the probe in FIG. 5, in the stage of use of FIG. 13.
Figure 14B:
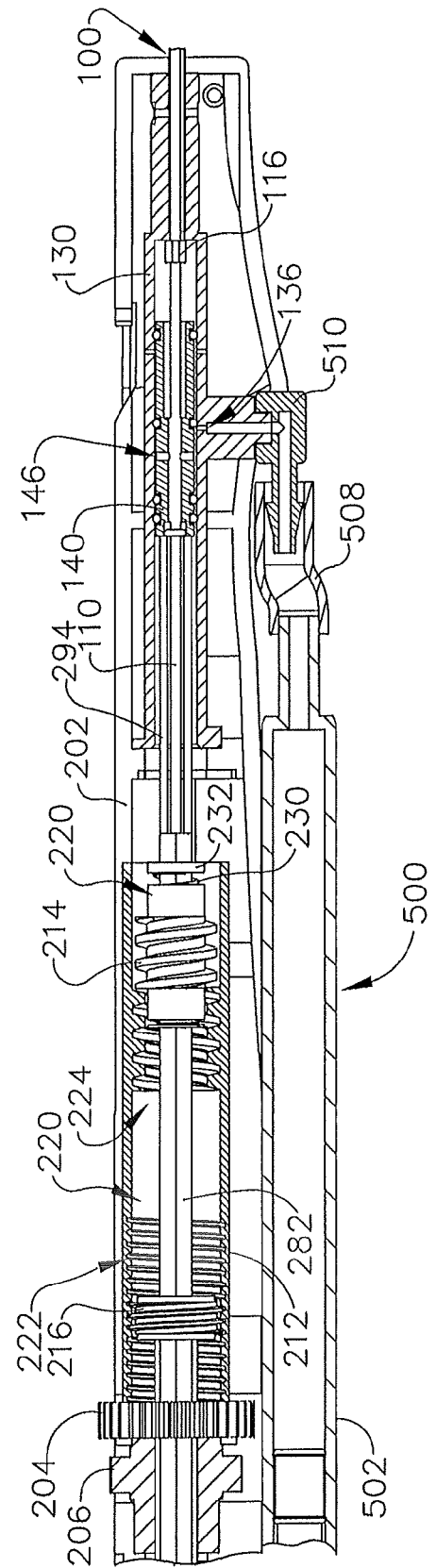
FIG. 14B depicts partial cross-sectional view of an intermediate region of the probe in FIG. 5, in the stage of use of FIG. 13.

In the present example, the configuration of drive nut (212), cutter lead screw (214), and plunger lead screw (216) is such that the length of drive nut (212) and its respective threaded portions (216, 218), combined with the position of cutter lead screw (214) and plunger lead screw (216), allows for a staged operability of cutter (110) and plunger (504). For instance, the length of drive nut (212) and the lengths of its threaded portions (216, 218) is such that when cutter lead screw (214) reaches the distal free-wheeling region (220) as shown in FIGS. 13-14, plunger lead screw (216) is still engaged with fine pitch region (222). Thus, drive nut (212) and plunger lead screw (216) are operable to continue translating plunger (504) despite cutter (110) translating no further distally, as can be seen in the transition from the operational stage shown in FIGS. 13-14 to the operational stage shown in FIGS. 15-16. In particular, FIGS. 13-14 show cutter (110) at the distal-most position with plunger (504) having additional distal range of travel; while FIGS. 15-16 show plunger (504) having translated further distally while cutter (110) remains at the distal-most position from FIGS. 13-14.

Also, the difference in the pitch of threaded regions (222, 224) of drive nut (212) provide for cutter lead screw (214) and plunger lead screw (216) to achieve different translational velocities. For instance, plunger lead screw (216) will have a slower translation velocity moving along the fine pitch region (222) compared to that of the cutter lead screw (214) moving along the coarse pitch region (224). In other words, while both cutter (110) and plunger (504) translate relative to drive nut (212), cutter (110) and plunger (504) translate at different rates, with cutter (110) translating faster than plunger (504). For instance, cutter lead screw (214) and cutter (110) translate a greater distance than plunger lead screw (216) and plunger (504) over the same time span since cutter lead screw (214) is associated with coarse pitch region (224) of drive nut (212), while plunger lead screw (216) is associated with fine pitch region (222). Since cutter overmold (280) translates unitarily with cutter (110), and since plunger lead screw (216), and arms (290) translate distally with plunger (504), and further since plunger lead screw (216) and arms (290) are slidable relative to cutter overmold (280), cutter overmold (280) translates distally relative to plunger lead screw (216) and arms (290) as cutter (110) and plunger (504) are being distally translated simultaneously. It should also be understood that a finer pitch for plunger lead screw (216) may provide increased mechanical advantage to plunger (504) as it translates. Other suitable configurations and relationships will be apparent to those of ordinary skill in the art in view of the teachings herein.

As noted above, distal ends (294) of arms (290) are operable to actuate shuttle valve slider (140) when plunger lead screw (216) advances distally. As best seen in FIGS. 8C, 10C, 12C, 14C, 16C, and 18C, shuttle valve slider (140) of the present example includes a wide bore region (142), a narrow bore region (144), and a pair of transverse openings (146) in fluid communication with narrow bore region (144). A shoulder (148) provides a transition from wide bore region (142) to narrow bore region (144). A plurality of o-rings (150) are positioned about the exterior of shuttle valve slider (140) and provide a seal against the inner sidewall defining hollow interior (132) of manifold (130). A stop member (116) is unitarily secured to cutter (110) and is movably positioned within wide bore region (142). Cutter (110) extends coaxially through bore regions (142, 144) of shuttle valve slider.

The outer diameter of cutter (110) and the inner diameters of bore regions (142, 144) are configured such that fluid may be communicated around the exterior of cutter (110) through each bore region (142, 144). Similarly, the outer diameter of stop member (116) and the inner diameter of wide bore region (142) are configured such that fluid may be communicated around the exterior of stop member (116) through wide bore region (142), even when stop member (116) is positioned within wide bore region (142). It should therefore be understood that transverse openings (146) are in fluid communication with the distal portion of the hollow interior (132) of manifold (130) via bore regions (142, 144), even with cutter (110) disposed through bore regions (142, 144) and with stop member (116) positioned within wide bore region (142). With the distal portion of hollow interior (132) being in further fluid communication with second lumen (122) of needle (100), it should also be understood that transverse openings (146) are thereby in fluid communication with second lumen (122) of needle (100). A seal (152) is positioned at the proximal end of narrow bore region (144), and seals against cutter (110) even when cutter (110) rotates and translates. Seal (152)

thus prevents fluid from escaping from within the interior of shuttle valve slider (140) through the proximal end of shuttle valve slider (140).

Figure 8C:
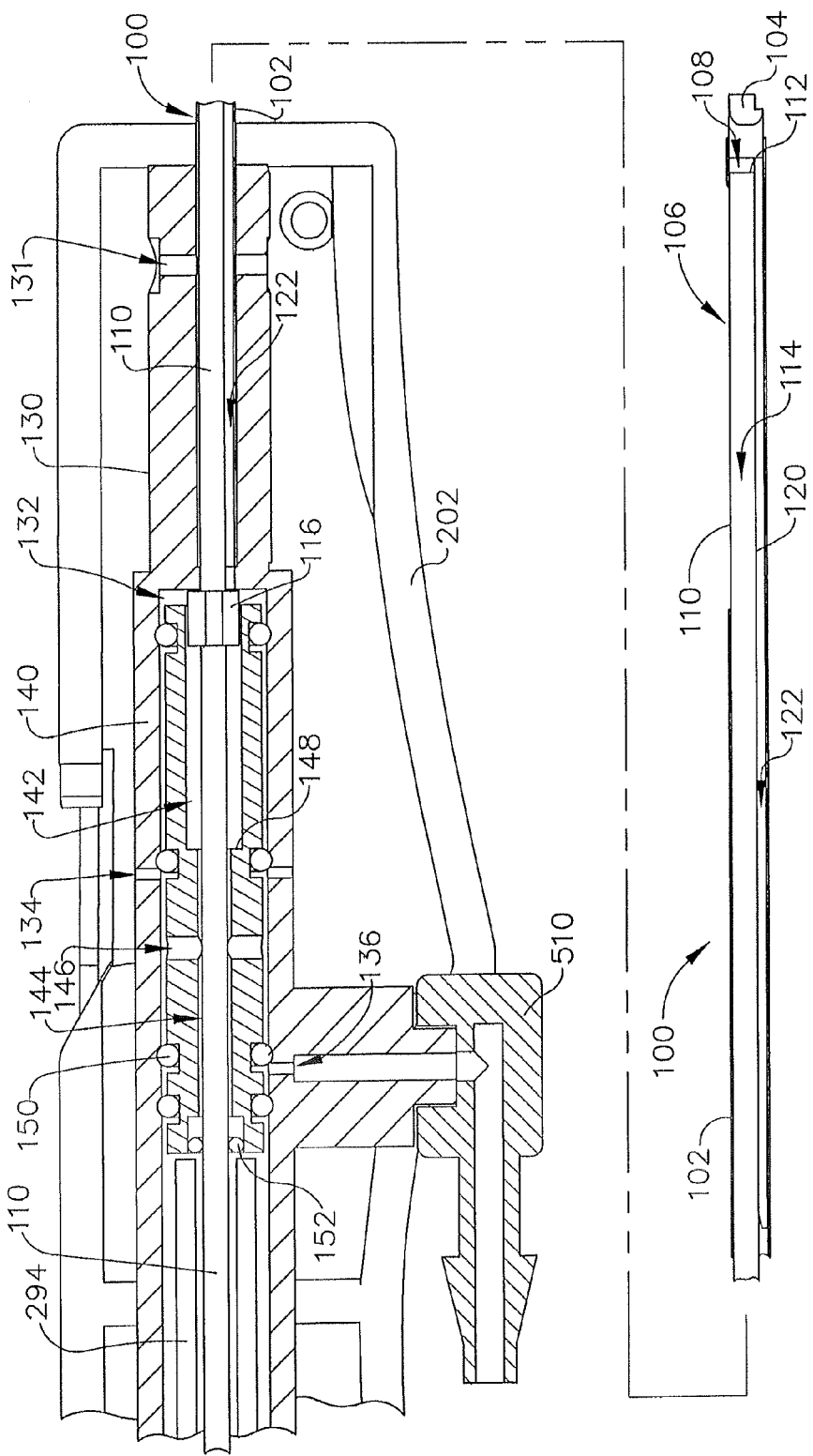
FIG. 8C depicts partial cross-sectional view of a distal region of the probe in FIG. 5, in the stage of use of FIG. 7.
Figure 10C:
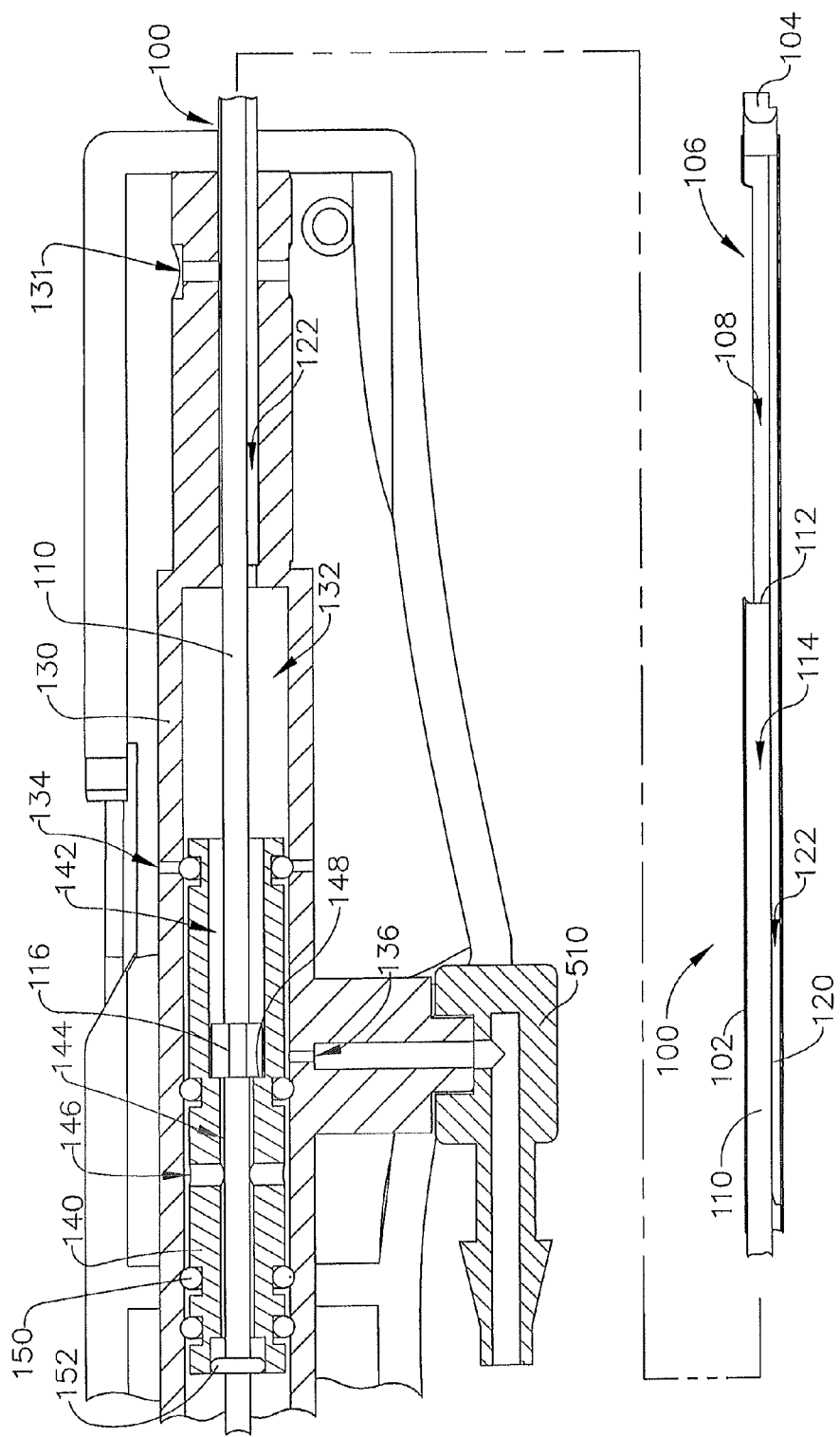
FIG. 10C depicts partial cross-sectional view of a distal region of the probe in FIG. 5, in the stage of use of FIG. 9.
Figure 12C:
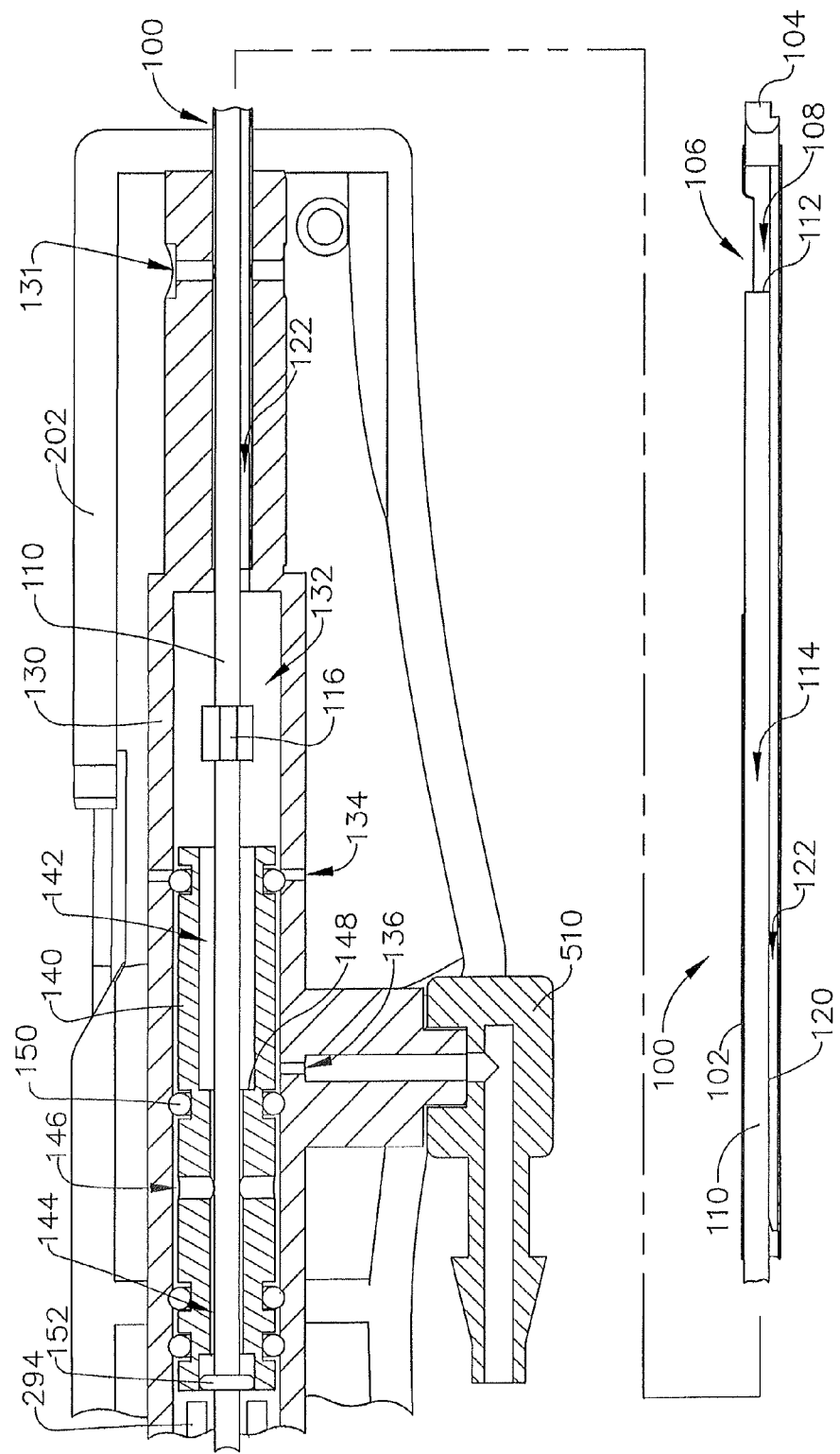
FIG. 12C depicts partial cross-sectional view of a distal region of the probe in FIG. 5, in the stage of use of FIG. 11.
Figure 14C:
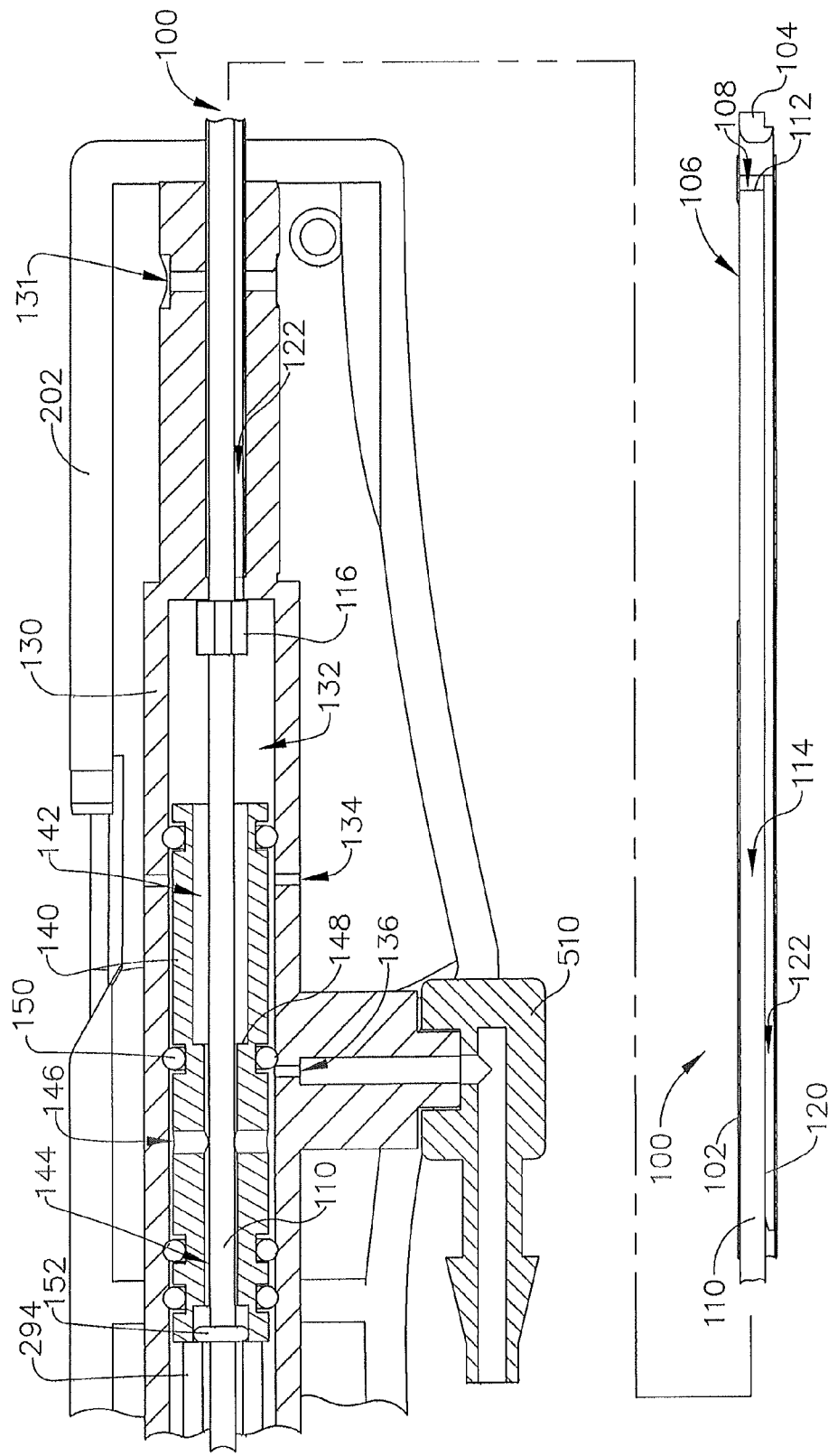
FIG. 14C depicts partial cross-sectional view of a distal region of the probe in FIG. 5, in the stage of use of FIG. 13.
Figure 15:
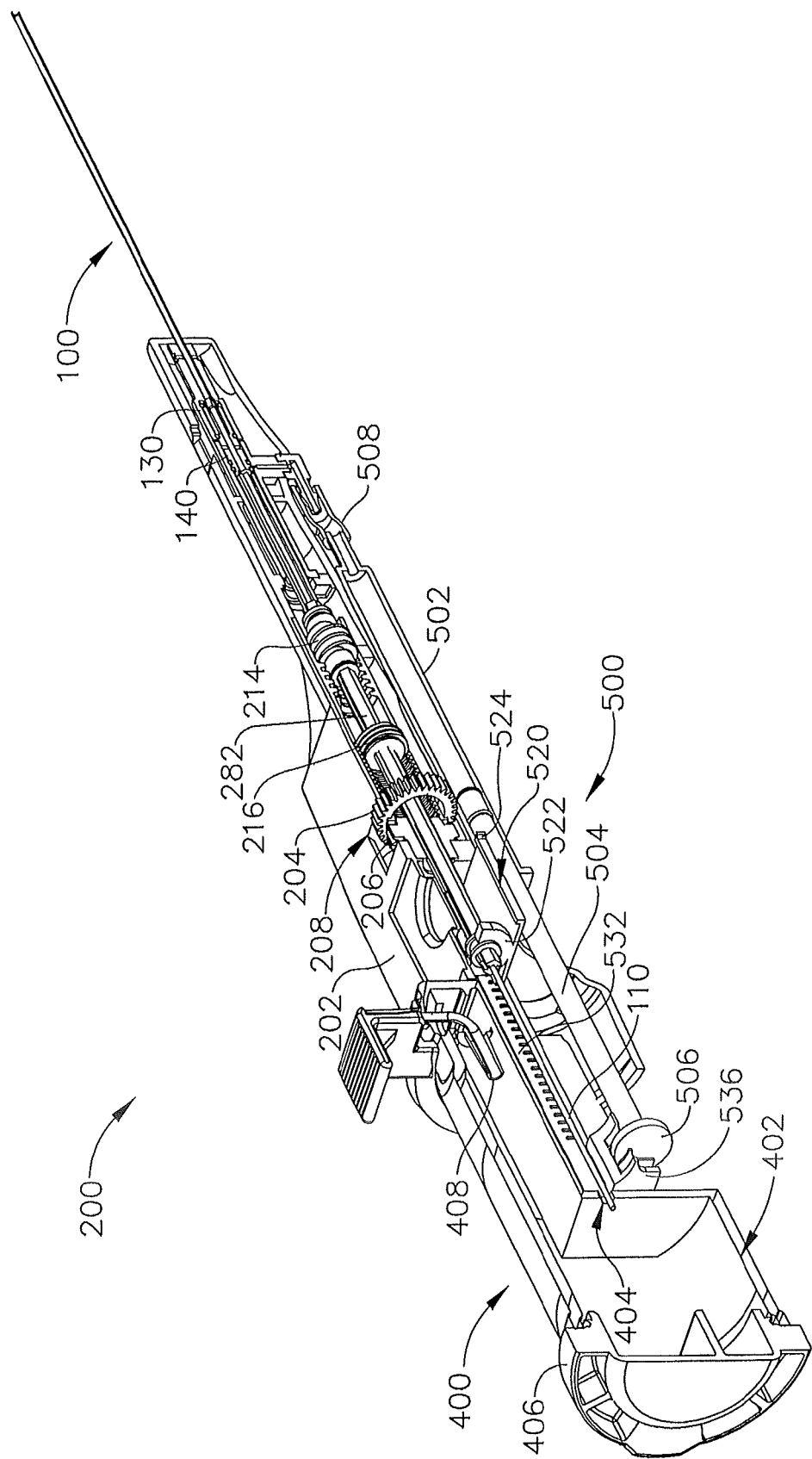
FIG. 15 depicts a perspective cross-sectional view of the probe of FIG. 5, with the probe being configured at a stage of use where the cutter and the valve assembly are both fully actuated, completing a first sampling cycle.
Figure 16A:
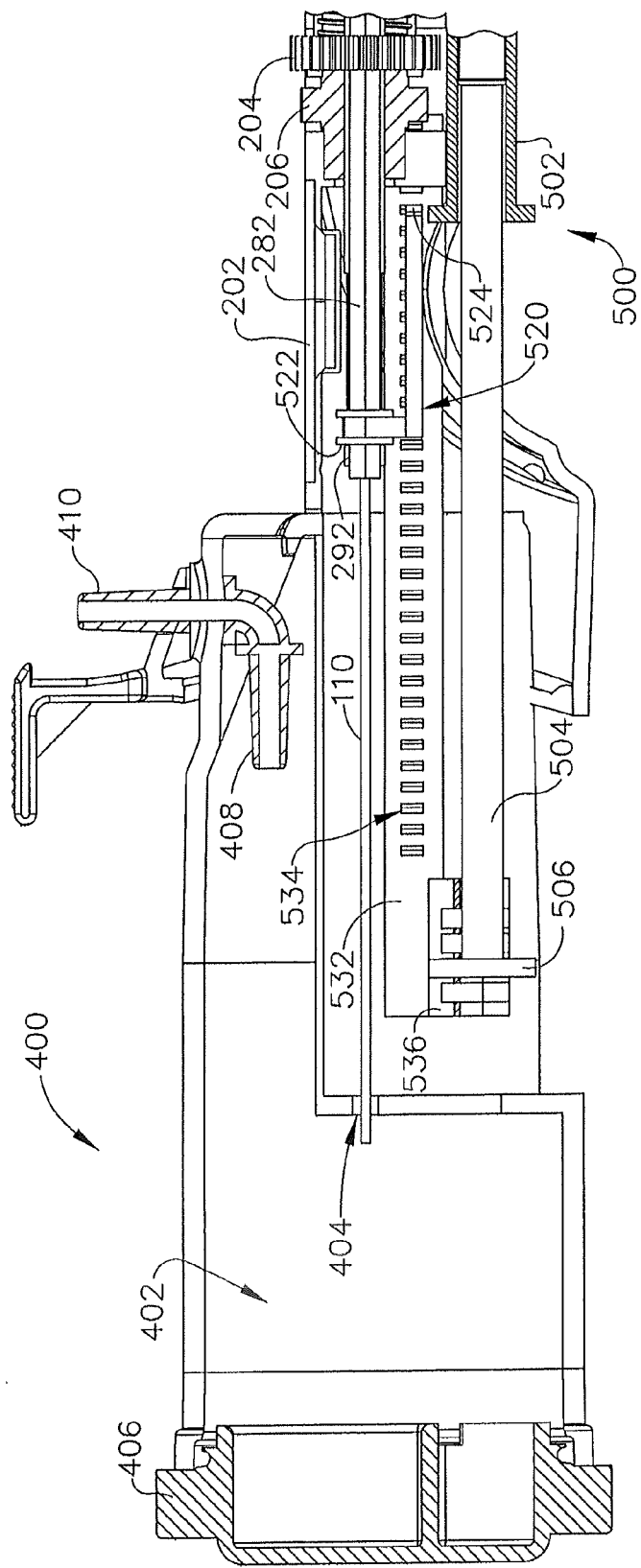
FIG. 16A depicts a partial cross-sectional view of a proximal region of the probe in FIG. 5, in the stage of use of FIG. 15.
Figure 16B:
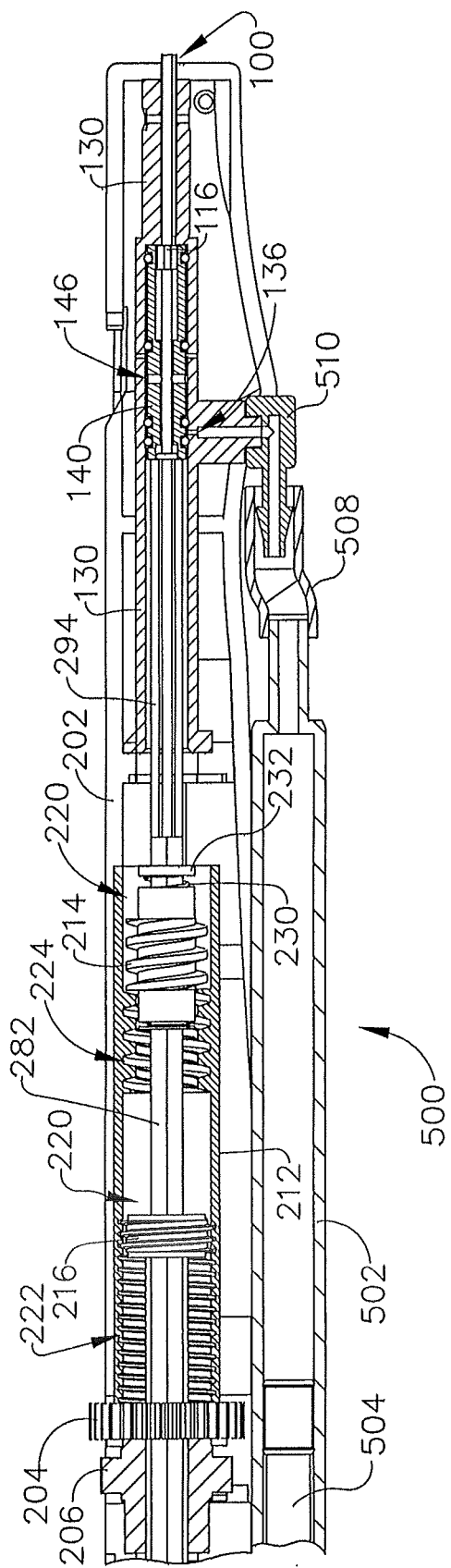
FIG. 16B depicts partial cross-sectional view of an intermediate region of the probe in FIG. 5, in the stage of use of FIG. 15.
Figure 16C:
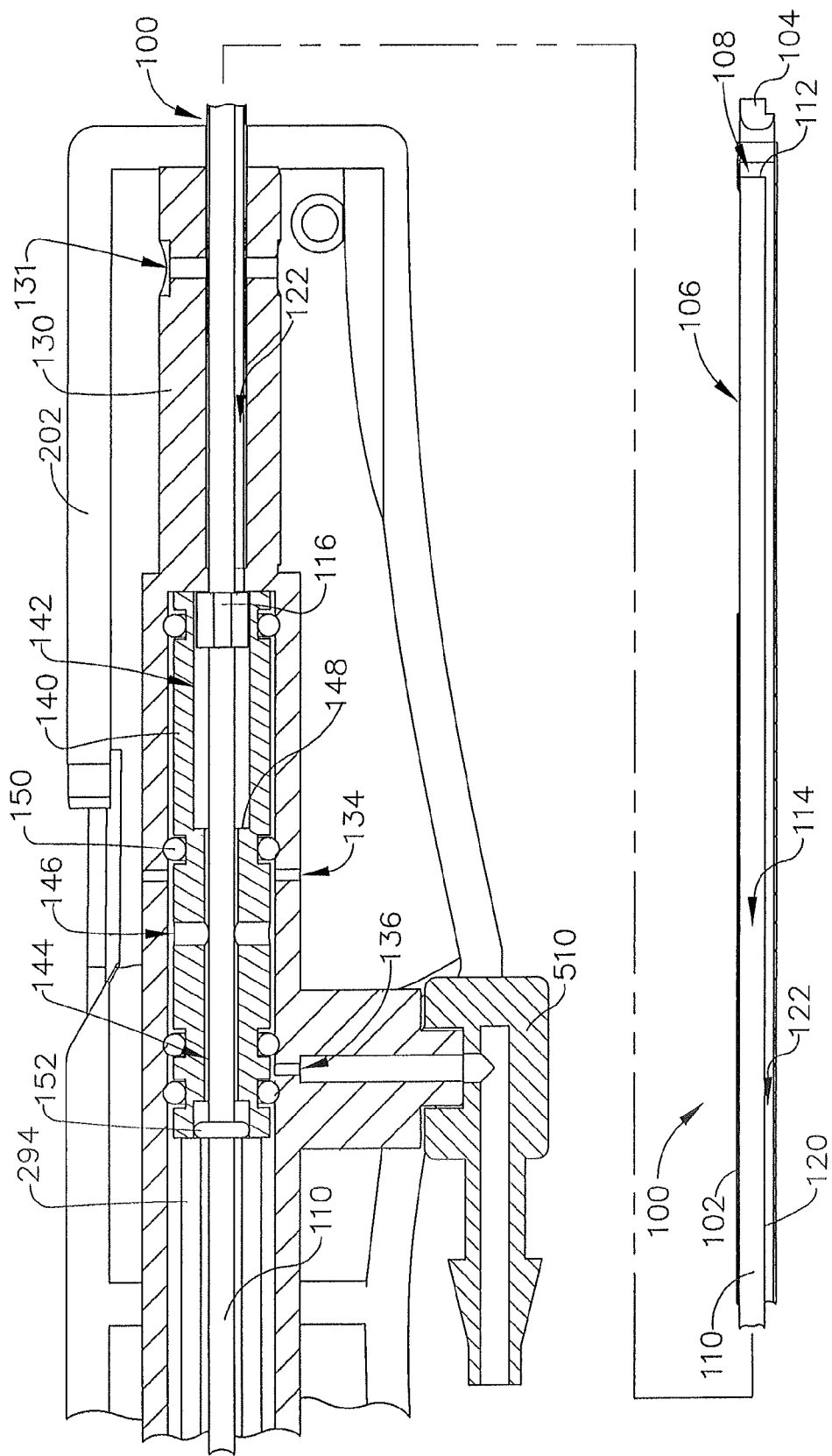
FIG. 16C depicts partial cross-sectional view of a distal region of the probe in FIG. 5, in the stage of use of FIG. 15.
Figure 17:
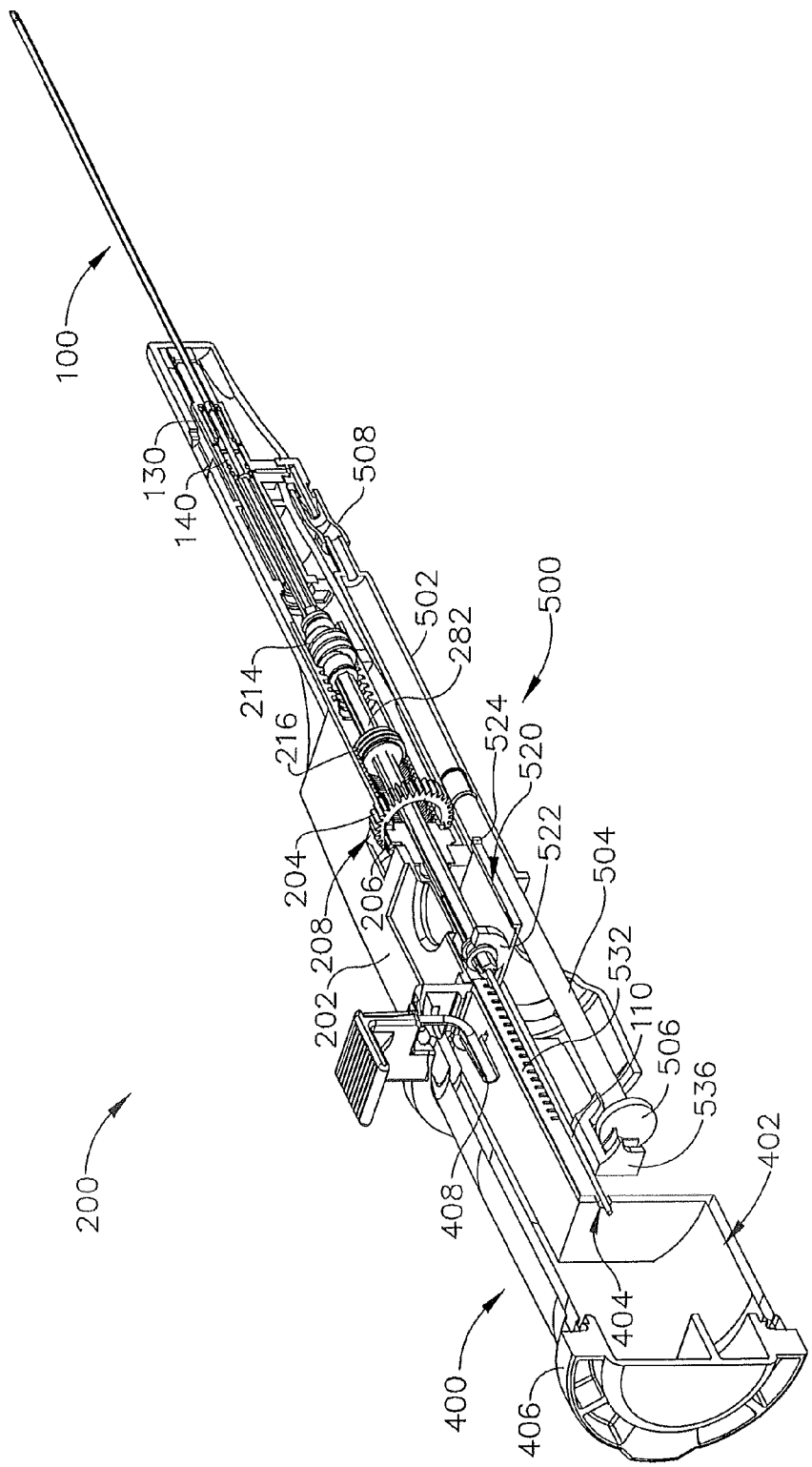
FIG. 17 depicts a perspective cross-sectional view of the probe of FIG. 5, with the probe being configured at a stage of FIG. 18A depicts a partial cross-sectional view of a proximal region of the probe in FIG. 5, in the stage of use of FIG. 17.
Figure 18A:
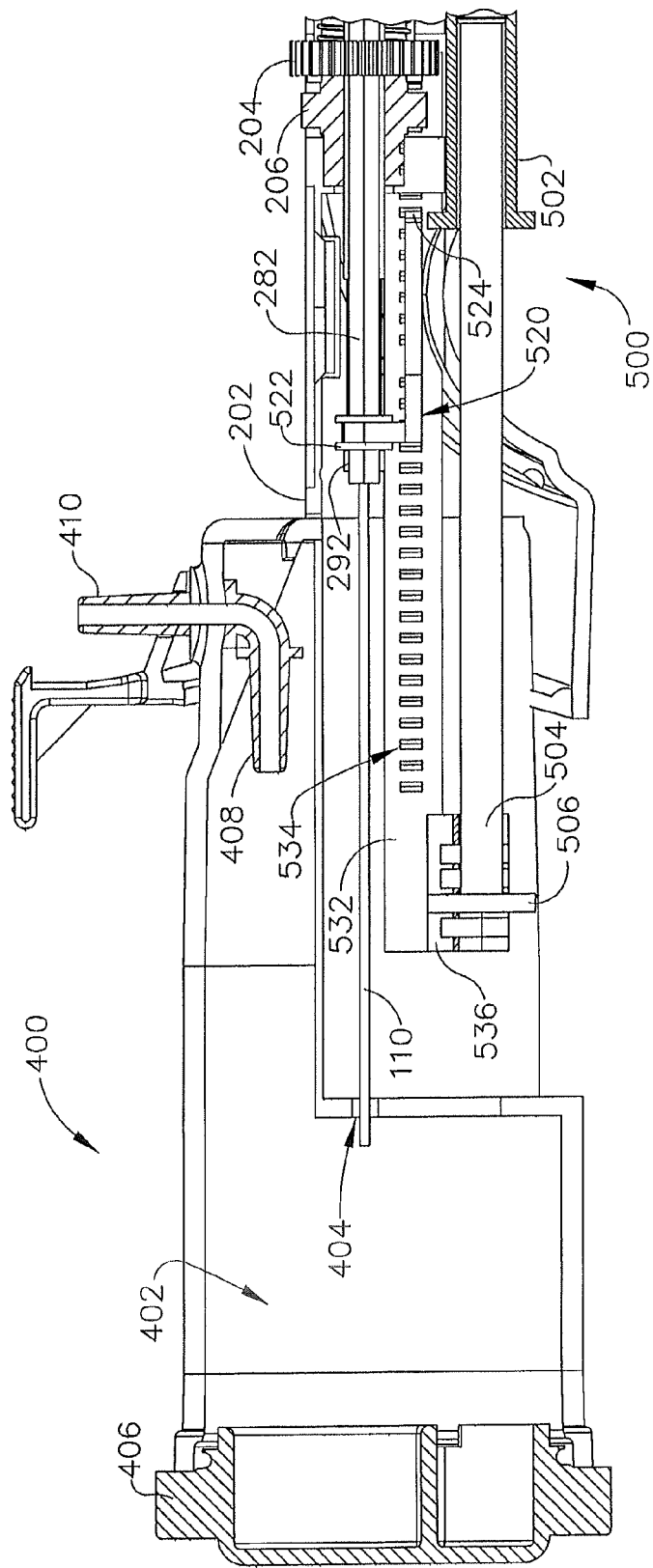
FIG. 18B depicts partial cross-sectional view of an intermediate region of the probe in FIG. 5, in the stage of use of FIG. 17.
FIG. 18C depicts partial cross-sectional view of a distal region of the probe in FIG. 5, in the stage of use of FIG. 17.
Figure 18B:
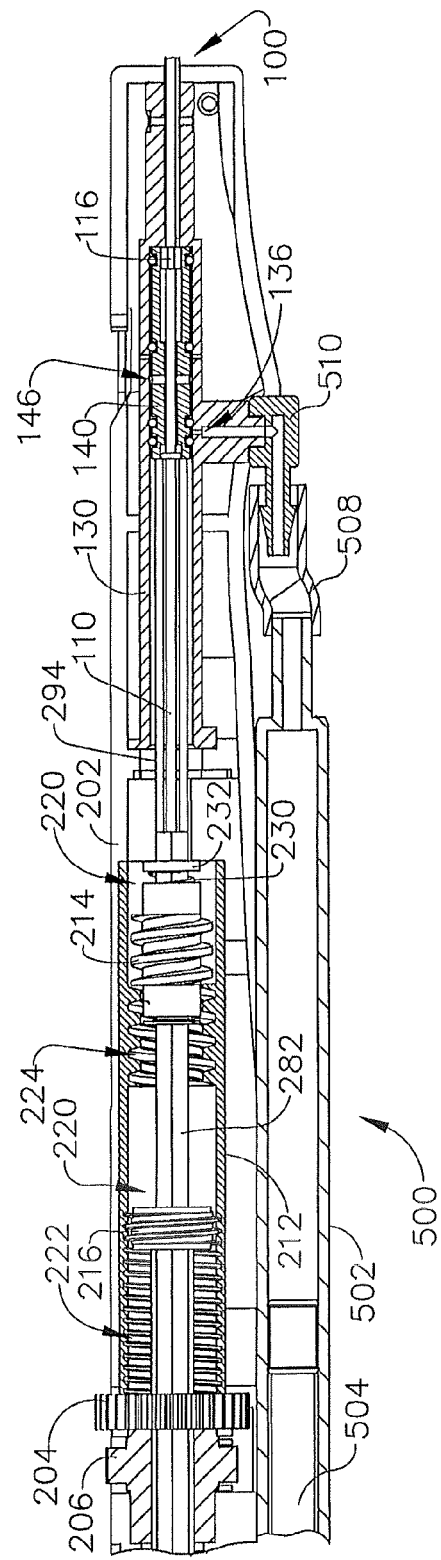
Figure 18C:
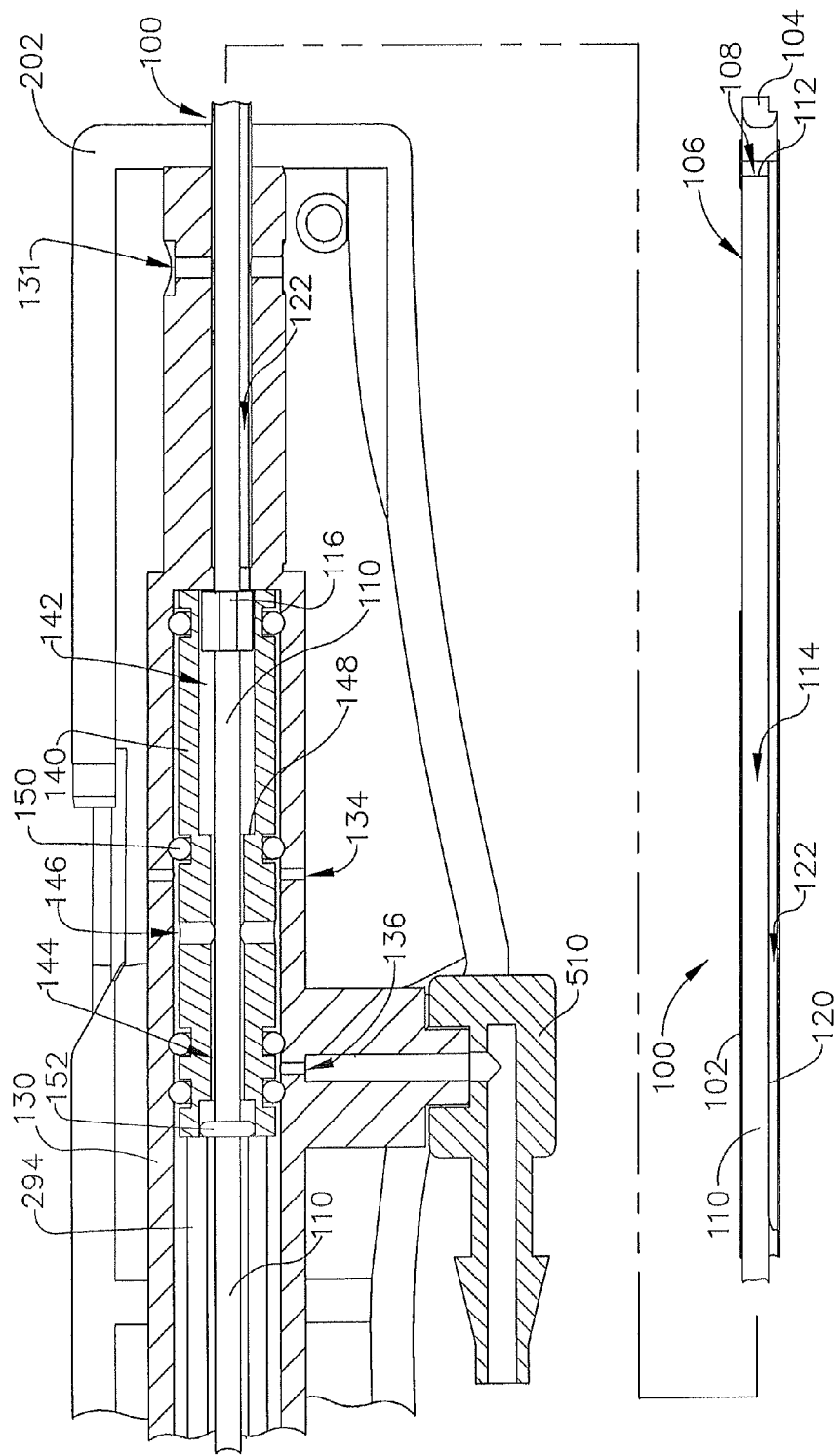

As best seen in FIGS. 8C, 10C, 12C, 14C, 16C, and 18C, shuttle valve slider (140) transitions between providing three different communicative states from transverse openings (146) to second lumen (122), based on the longitudinal position of cutter (110). That is, shuttle valve slider (140) provides communication of atmospheric air from openings (134) to second lumen (122) via transverse openings (146) during stages of operation as depicted in FIGS. 8C, 16C, and 18C. Shuttle valve slider (140) seals second lumen (122) relative to openings (134, 136) during stages of operation as depicted in FIGS. 10C and 12C. Shuttle valve slider (140) provides communication of saline from opening (136) to second lumen (122) via transverse openings (146) during stages of operation as depicted in FIG. 14C. This action of shuttle valve slider (140) will be discussed in relation to operation of other components of probe (200) in greater detail below.

D. Exemplary Cooperation between Components of Needle, Cutter Actuation Mechanism, and Syringe Actuation Mechanism In FIGS. 7 and 8A-8C, cutter (110) is in a distal position, effectively closing lateral aperture (106) of needle (100). Shuttle valve slider (140) is positioned distally in manifold (130), thereby venting atmospheric air to second lumen (122). At this stage, needle (100) is inserted in the patient's prostate (or other location in the patient's anatomy) for tissue sampling. Once lateral aperture (106) is positioned at the desired biopsy site, gears (204, 206) are then rotated in a first direction by gears (304, 306) as will be described in greater detail below. As shown in FIGS. 9 and 10A-10C, this rotation of gears (204, 206, 304, 306) causes cutter (110) to translate proximally through cooperation between drive nut (212) and cutter lead screw (214), as described above. This proximal translation of cutter (110) effectively opens lateral aperture (106) of needle (100) (see FIG. 10C). Relative rotation between plunger lead screw (216) and drive nut (212) also causes plunger lead screw (216) to translate proximally (see FIG. 10B) and thereby causes arms (290) to translate proximally (see FIG. 10A). However, latching feature (292) translates proximally relative to yoke (522) of ratcheting member (520) through a range of "lost motion," then arms (290) push ratcheting member (520) proximally just slightly at the proximal-most range of travel by latching feature (292) and arms (290). In particular, arms (290) push ratcheting member (522) proximally by just one slot (534) of actuation frame (530).

As best seen in FIG. 10B, cutter lead screw (214) is positioned in a proximal free-wheeling region (220) of drive nut (212) at this stage, with proximal coil spring (234) biasing cutter lead screw (214) distally toward coarse pitch region (224) of drive nut (212). Cutter (110) is thus at a proximal-most position. The proximal movement of cutter (110) causes stop member (116) to translate proximally. During this proximal movement of stop member (116), stop member (116) eventually engages shoulder (148) within shuttle valve slider (140) and thereby pushes shuttle valve slider (140) proximally. With shuttle valve slider (140) in this proximal position, o-rings (150) seal transverse openings (146) relative to openings (134) and relative to opening (136). Second lumen (122) is thus sealed relative to atmospheric air and relative to saline at this stage. As will be described in greater detail below, a vacuum pump (310) in holster (300) draws a vacuum through lumen (114) of cutter (110) while cutter (110) is retracted from the position shown in FIGS. 7 and 8A-8C to the position shown in FIGS. 9 and 10A-10C. Vacuum pump (310) continues to draw this vacuum through lumen (114) of cutter (110) while cutter (110) is in the position shown in FIGS. 9 and 10A-10C, such that the vacuum assists in drawing tissue into opened lateral aperture (106) of needle (100).

After lateral aperture (106) has been opened as described above, the direction of rotation of gears (204, 206, 304, 306) is reversed. This reversal causes cutter (110) to start advancing distally through cooperation between drive nut (212) and cutter lead screw (214). As cutter (110) advances, sharp distal edge (112) of cutter (110) begins to sever tissue protruding through aperture (106). FIGS. 11 and 12A-12C show cutter (110) in a partially advanced position during this distal range of travel. Relative rotation between plunger lead screw (216) and drive nut (212) also causes plunger lead screw (216) to translate distally (see FIG. 12B) thereby causes arms (290) to translate distally (see FIG. 12A). However, latching feature (292) translates distally relative to yoke (522) of ratcheting member (520) through a range of "lost motion." Ratcheting member (522) thus remains stationary at this stage. As best seen in FIG. 12C, shuttle valve slider (140) also remains stationary during part of the distal range of motion of cutter (110). In particular, stop member (116) leaves shoulder (148) without pulling shuttle valve slider (140). Distal ends (294) of arms (290) move distally toward the proximal end of shuttle valve slider (140) but have not yet engaged shuttle valve slider (140) at this stage. Thus, second lumen (122) remains sealed relative to atmospheric air and relative to saline at this stage. In addition, vacuum pump (310) continues to draw a vacuum through lumen (114) of cutter (110) at this stage.

FIGS. 13 and 14A-14C show a stage where cutter (110) has reached a distal-most position yet shuttle valve slider (140) is still moving distally. In particular, cooperation between drive nut (212) and cutter lead screw (214) have caused cutter (110) to advance distally, with cutter lead screw (214) being positioned in a distal free-wheeling region (220) of drive nut (212) at this stage as best seen in FIG. 14B. Cutter (110) thus remains longitudinally stationary at this stage while cutter (110) continues to rotate. Distal coil spring (230) biases cutter lead screw (214) proximally toward coarse pitch region (224) of drive nut (212), such that cutter (110) will once again translate proximally as soon as the direction of rotation of gears (204, 206, 304, 306) is again reversed. It should be understood that, with cutter (110) having translated from a proximal-most position to a distal-most position, sharp distal edge (112) of cutter (110) has severed a tissue sample (not shown) from tissue protruding through aperture (106).

As shown in FIG. 14A, while drive nut (212) and arms (290) continue to translate distally, latching feature (292) also continues to translate distally relative to yoke (522) of ratcheting member (520) through a range of "lost motion." Ratcheting member (522) thus continues to remain stationary at this particular stage. Distal ends (294) of arms (290) have engaged the proximal end of shuttle valve slider (140) and have pushed shuttle valve slider (140) distally at this stage. In particular, as best seen in FIG. 14C, shuttle valve slider (140) has been pushed distally to a position where transverse openings (146) are in fluid communication with opening (136); while transverse openings (146) are sealed relative to openings (134) by o-rings (150). Second lumen (122) is thus in fluid communication with saline yet is sealed relative to atmospheric air at this stage.

As shown in the transition from FIGS. 13 and 14A-14C to FIGS. 15 and 16A-16C, gears (204, 206, 304, 306) continue to rotate such that plunger lead screw (216) continues to translate distally while cutter lead screw (214) continues to remain longitudinally stationary. As best seen in FIG. 16A, latching feature (292) has finally engaged yoke (522) and has thereby pulled yoke (522) distally. This distal movement of yoke (522) causes actuation frame (530) to translate distally, which in turn urges plunger (504) distally to expel saline distally from barrel (502). This saline is further communicated to manifold (130) via conduit (508), coupling (510), and opening (136). As shown in FIG. 16C, distal ends (294) of arms (290) have pushed shuttle valve slider (140) to a distal-most position at this stage. In this position, transverse openings (146) are in fluid communication with openings (134); while transverse openings (146) are sealed relative to opening (136) by o-rings (150). Second lumen (122) is thus in fluid communication with atmospheric air yet is sealed relative to saline at this stage. However, it should be understood that during part of the transition from the positions shown in FIGS. 13 and 14A-14C to FIGS. 15 and 16A-16C, second lumen (122) will be in fluid communication with saline as plunger (504) is being pushed distally. Thus, with cutter (110) in a distal position and with a severed tissue sample being captured within the distal end of lumen (114) of cutter (110), a bolus of saline (of a predetermined volume) is initially communicated to the distal face of the severed tissue sample via second lumen (122) and then atmospheric air is communicated behind the saline (e.g., such that the bolus of saline is between the severed tissue sample and the atmospheric air). Since vacuum continues to be communicated through lumen (114) of cutter (110) this whole time, the pressure differential acting against the severed tissue sample draws the severed tissue sample proximally through lumen (114) of cutter (110) and into tissue collection chamber (400).

After the above described components have reached the configuration shown in FIGS. 15 and 16A-16C, the direction of rotation of gears (204, 206, 304, 306) may again be reversed repeatedly until the desired number of tissue samples have been acquired. Each time cutter (110) is actuated through a full cycle of proximal retraction and distal advancement, plunger (504) is advanced distally in increments to repeatedly communicate a bolus of saline to manifold (130). For instance, FIGS. 17 and 18A-18C show probe (200) after cutter (110) has been actuated through a second cutting cycle. Thus, all components at this stage are in the same positions as shown in FIGS. 15 and 16A-16C, except that latching feature (292) has pulled yoke (522) further distally (compare FIG. 16A with FIG. 18A). This further distal movement of yoke (522) causes actuation frame (530) to translate further distally, which in turn urges plunger (504) distally to expel another bolus of saline distally from barrel (502). Of course, it should be understood that saline and/or various other fluids may be communicated to manifold (130) in various other ways.

It should be understood that the above described components and operations for actuating syringe (500) and for providing selective fluid communication to second lumen (122) are merely illustrative examples. Other suitable alternative versions, features, components, configurations, and operations for providing such functionality will be apparent to those of ordinary skill in the art in view of the teachings herein. It should also be understood that syringe (500) and/or selective fluid communication to second lumen (122) may be simply omitted, if desired.

E. Exemplary Tissue Collection Chamber

Tissue collection chamber (400) of the present example is removably coupled with the proximal portion of probe (200). Tissue collection chamber (400) defines a hollow interior (402) that is configured to receive tissue samples. In particular, the proximal end of cutter (110) is received in hollow interior (402) via an opening (404), such that severed tissue samples are deposited directly into interior (402) from the lumen (114) of cutter (110). A removable cap (406) provides ready access to interior (402) for retrieval of biopsy samples. A vacuum port (408) is also in fluid communication with interior (402), such that vacuum port (408) is operable to communicate a vacuum to interior (402). Vacuum port (408) is also in fluid communication with an external vacuum port (410). Vacuum port (410) is configured to receive a vacuum generated from within holster (300) by vacuum pump (310) as will be described in greater detail below, though it should be understood that vacuum may be provided by an external source in addition to or in lieu of being provided by a source in holster (300). It should also be understood that a vacuum communicated to interior (402) will be further communicated to cutter lumen (114). Such a vacuum in cutter lumen (114) may assist in drawing tissue into lateral aperture (106) as noted above. Such a vacuum in cutter lumen (114) also assists in drawing severed tissue samples proximally through cutter (110) as described above, for deposit into tissue collection chamber (400). Cap (406) may provide a sufficient seal so as to not compromise a vacuum in interior (402) during operation of device (10).

Tissue collection chamber (400) may be fitted with a drain plug or other type of feature to permit periodic draining of fluid collected within hollow interior (402). As another merely illustrative alternative, a hydrophilic material or other absorbent material may be provided within hollow interior (402) to soak up saline and/or other fluids. In some versions, a basket or tray is provided within interior (402). Such a tray may be configured to receive and hold tissue samples yet may also be configured to allow fluids to pass therethrough. By way of example only, tissue collection chamber (400) may be constructed in accordance with at least some of the teachings of U.S. Pub. No. 2010/0317997. Alternatively, tissue collection chamber (400) may be constructed in accordance with at least some of the teachings of U.S. Provisional Patent App. No. 61/381,466, entitled "Biopsy Device Tissue Sample Holder with Removable Basket," filed Sep. 10, 2010, the disclosure of which is incorporated by reference herein. As another merely illustrative example, tissue collection chamber (400) may include a plurality of discrete tissue sample chambers. For instance, tissue collection chamber (400) may be constructed in accordance with at least some of the teachings of U.S. Pub. No. 2008/0214955. Alternatively, tissue collection chamber (400) may be constructed in accordance with at least some of the teachings of U.S. Pub. No. 2008/0221480, entitled "Biopsy Sample Storage," published Sep. 11, 2008, the disclosure of which is incorporated by reference herein. Still other suitable ways in which tissue collection chamber (400) may be constructed and operable will be apparent to those of ordinary skill in the art in view of the teachings herein. Similarly, other suitable features, components, configurations, and operabilities that may be provided by probe (200) will be apparent to those of ordinary skill in the art in view of the teachings herein.

III. Exemplary Holster

As noted above, holster (300) of the present example includes a housing (302), exposed gears (304, 306), and a vacuum pump (310). As noted above, gear (304) acts as a cutter translation drive gear while gear (306) acts as a cutter rotation drive gear. Holster (300) further includes a motor (312), a battery (not shown) that is operable to power motor (312), and an actuation button (314) that is operable to selectively activate motor (312). The battery may be rechargeable via any suitable recharging features. Alternatively, the battery may be non-rechargeable. The battery may comprise one or more alkaline batteries, one or more nickel-cadmium batteries, one or more lithium-ion batteries, and/or any other suitable battery type. In some other versions, motor (312) receives power from an external source (e.g., via a wire), in addition to or in lieu of a battery being included. It should also be understood that holster (300) may include one or more printed circuit boards and/or control modules, etc., including components, firmware, etc. that is/are operable to execute control algorithms via motor (312). Other suitable electrical components for holster (300) will be apparent to those of ordinary skill in the art in view of the teachings herein.

As another merely illustrative variation, motor (312) may include an impeller responsive to pressurized air or some other type of pressurized medium. It should also be understood that cutter (110) and/or plunger (504) may be driven by a pneumatic motor and/or actuator, a hydraulic motor and/or actuator, or a variety of other types of components. Various other suitable driving means, as well as various suitable ways in which such driving means may be incorporated into device (10), will be apparent to those of ordinary skill in the art in view of the teachings herein.

A drive shaft (320) extends from motor (312), and motor (312) is operable to selectively rotate drive shaft (320) in either direction. A driving gear (322) is positioned about drive shaft (320), such that rotation of drive shaft (320) rotates driving gear (322). Driving gear (322) meshes with driven gear (324), which is secured to a second shaft (326). Second shaft (326) is in communication with vacuum pump (310), such that rotation of second shaft (326) causes vacuum pump (310) to generate a vacuum. Vacuum pump (310) of the present example comprises a conventional diaphragm pump. In particular, second shaft (326) is coupled with an eccentric disk (not shown—e.g., a device for converting circular motion into rectilinear motion, comprising a disk fixed off-center to second shaft (326)), which is configured to cause a rod (not shown—e.g., the rod may be coupled with or otherwise driven by the eccentric disk) of vacuum pump (310) to reciprocate as motor (312) and shafts (309, 322) rotate. This rod of vacuum pump (310) drives a diaphragm (not shown) of vacuum pump (310) as the rod reciprocates, causing vacuum pump (310) to induce a vacuum. When probe (200) and holster (300) are coupled together, vacuum port (410) enters opening (308) formed in housing (302) near vacuum pump (310). In some versions, a coupling (not shown) at opening (308) provides an automatic fluid coupling between vacuum port (410) and vacuum pump (310) as soon as probe (200) is coupled with holster (300). In some other versions, a separate conduit (not shown) is used to couple vacuum port (410) with vacuum pump (310). Other suitable ways for coupling vacuum port (410) with vacuum pump (310) will be apparent to those of ordinary skill in the art in view of the teachings herein. It should also be understood that vacuum pump (310) of the present example operates in the same way regardless of which direction motor (312) rotates. Of course, any other suitable type of vacuum source may be used, including a vacuum source that is external to biopsy device (10).

A third gear (328) is also unitarily secured to second shaft (326), such that third gear (328) rotates unitarily with second shaft (326). Third gear (328) meshes with fourth gear (330), which is unitarily secured to a third shaft (332). A fifth gear (334) is also unitarily secured to third shaft (332). Fifth gear (334) meshes with gear (306) referred to above. Gears (306, 304) are unitarily secured to a common shaft (not shown). It should be understood from the foregoing that activation of motor (312) causes gears (304, 306) to rotate simultaneously while also activating vacuum pump (310) to generate a vacuum. As noted above, rotation of gears (304, 306) causes rotation of gears (204, 206), which in turn causes simultaneous rotation and translation of cutter (110) as well as translation of plunger (504). It should therefore be understood that, with such configurations as described, motor (312) is capable of simultaneously operating vacuum pump (310), rotating and translating cutter (110), and translating plunger (504). Of course device (10) could also be configured such that more than one motor (312) may be used to operate these components.

IV. Exemplary Operation and Use

In use, device (10) is operably configured to sever biopsy tissue samples from a tissue specimen (e.g., within an adult human prostate and/or some other location in a patient's anatomy). Device (10) may come from the manufacturer as a ready-to-use unit or it may come in components that may be assembled by a user. Where device (10) comprises a series of components assembled by a user, the components may be connectable by any suitable means. For example, probe (200) and holster (300) may be configured with snap-fitting connections. Similarly, tissue collection chamber (400) may snap-fit with probe (200) or may screw into probe (200) as described above. Needle (100) may be integral with probe (200) or needle (100) may screw into or snap-fit with probe (200). Various suitable ways in which the components of device (10) may be assembled and/or disassembled will be apparent to those of ordinary skill in the art in view of the teachings herein.

Once device (10) is assembled and ready for use, it may be inserted into a patient's tissue to collect one or more biopsy samples. In an initial position, cutter (110) is advanced distally to close off lateral aperture (106) of cannula (102), as shown in FIGS. 7 and 8A-8C. Needle (100) is then inserted into the patient's tissue. After needle (100) is located by the user in a desired position relative to the tissue of interest in the patient, actuation button (314) may be depressed to begin the collection of a biopsy sample from the patient's tissue. In response to actuation button (314) being depressed, motor (312) begins to rotate gears (304, 306) in a first direction and also rotate second shaft (326) to activate vacuum pump (310). As described above, the rotation of gear (304) ultimately causes cutter (110) to translate within cannula (102). With gear (304) being rotated in the first direction, cutter (110) translates proximally to open lateral aperture (106) as shown in FIGS. 9 and 10A-10C. At this stage, plunger (504) is also at a proximal position.

With lateral aperture (106) open, the vacuum generated by vacuum pump (310) is communicated through ports (408, 410) of tissue collection chamber (400) into hollow interior (402) and ultimately through lumen (114) of cutter (110). The vacuum thereby delivered to lateral aperture (106) may be sufficient to cause a portion of the patient's tissue to prolapse through lateral aperture (106) and into needle (100).

Once tissue is within needle (100), upon full retraction of cutter (110), motor (312) may reverse direction, rotating now in a second direction. This direction reversal of motor (312) may cause gears (304, 306) to also rotate in a second direction. Such rotation of gears (304, 306) in the second direction ultimately causes cutter (110) to rotate and translate distally within needle (100), thereby advancing cutter (110) to close off lateral aperture (106) as shown in FIGS. 13 and 14A-14C and sever a biopsy sample from the patient's tissue protruding through lateral aperture (106). Such rotation of gears (304, 306) in the second direction also eventually causes plunger (504) to translate distally as shown in FIGS. 15 and 16A-16C. As shown in the transition from FIGS. 11 and 12A-12C to FIGS. 15 and 16A-16C, plunger (504) trails behind cutter (110) as they both advance distally. During this process, rotation of motor (312) continues to activate vacuum pump (310) to draw a vacuum through lumen (114) of cutter (110). As noted above, vacuum pump (310) operates in the same fashion regardless of which direction second shaft (326) is rotated in.

As cutter (110) reaches a distal-most position, as shown in FIGS. 13 and 14A-14C, cutter lead screw (214) reaches distal free-wheeling region (220) of drive nut (212), such that cutter (110) ceases further distal translation, yet continues to rotate. In the meantime, plunger (504) eventually advances distally with continued differential rotation of drive nut (212) and cutter overmold (280) and resulting distal movement of plunger lead screw (216). In addition, shuttle valve slider (140) is eventually pushed distally, such that saline is communicated to second lumen (122) and then atmospheric air is communicated to second lumen (122). With vacuum pump (310) continuing to draw a vacuum through lumen (114) of cutter (110), saline and atmospheric air to second lumen (122) provide a pressure differential to promote proximal transport of the severed tissue sample through lumen (114) of cutter (110) and into tissue collection chamber (400). It should be noted that any other suitable fluid may be used instead of saline, including but not limited to other liquids, pressurized air, atmospheric air, etc.

When device (10) reaches the stage shown in FIGS. 15 and 16A-16C, the sample cycle may be considered complete. Once complete, the sample cycle may be repeated to gather additional tissue samples if so desired (e.g., up to 25-35 times or more). This may be accomplished by repositioning the already inserted device (10), e.g. by altering the depth and lateral aperture (106) orientation, such that removal and reinsertion is not required to harvest multiple tissue specimens from a patient. It should also be understood that a plurality of tissue samples may be gathered with just a single insertion of needle (100) without necessarily having to reposition needle (100) within the patient between acquisition of each tissue sample. The rotational direction of motor (312) may be reversed to retract cutter (110) and ratcheting member (520) proximally; then be reversed again to advance cutter (110) and plunger (504) distally for additional cycles. Once a desired number of tissue samples been collected, the severed tissue samples may be retrieved from tissue collection chamber (400) by removing end cap (406).

It should be understood that the above-described use is merely one example of a way in which device (10) may be used. Various other suitable ways in which device (10) may be used will be apparent to those of ordinary skill in the art in view of the teachings herein.

It should also be understood that, through the use of a clutch or other structure, device (10) may be operably configured such that cutter (110) only rotates upon distal translation and not also proximal translation. Also, based on the teachings herein, those of ordinary skill in the art will appreciate that motor (312) may change rotation automatically upon full retraction of cutter (110) as described, or user controls may be included to permit motor (312) rotation direction to be dictated by the user, e.g. via a directional switch or other suitable features. Furthermore, in some versions of device (10), motor (312) simply rotates only in one direction.

Versions of biopsy devices described herein may be actuated electromechanically, e.g., using one or more electrical motors, solenoids, etc. However, other actuation modes may be suitable as well, e.g., pneumatically, and/or hydraulically. Such alternative actuation modes may be combined with electromechanical actuation or may be provided in lieu of electromechanical actuation. Various suitable ways in which such alternative forms of actuation may be provided in a device as described herein will be apparent to those of ordinary skill in the art in view of the teachings herein.

Versions of biopsy devices described herein may have various types of construction. By way of example only, any of the devices described herein, or components thereof, may be constructed from suitable metals, ceramics, plastics, or combinations thereof. Furthermore, although not required, the construction of devices described herein may be compatible with or optimize their use with various imaging technologies. For instance, a device adapted for use with MRI may be constructed from all non-ferromagnetic materials. As another merely illustrative example, when using optional imaging technologies with devices described herein, certain adaptations may include modifications to materials of construction such that portions or the device may readily appear in a resultant image. For instance, it may be desirable to have the side aperture of a needle appear visible in an image to confirm suitable placement of the device before capturing a tissue sample. Various suitable ways in which these and other modifications to the construction of devices described herein will be apparent to those of ordinary skill in the art in view of the teachings herein.

Versions of the biopsy devices described above may have application in conventional medical treatments and procedures conducted by a medical professional, as well as application in robotic-assisted medical treatments and procedures.

Versions of the biopsy devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application. It should also be understood that certain parts of a device may be reconditioned for subsequent reuse while other parts of the same device may simply be disposed of after a first use.

Versions of the devices described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

While several examples of biopsy devices and components thereof have been discussed in detail above, it should be understood that the components, features, configurations, and methods of using the devices discussed are not limited to the contexts provided above. In particular, components, features, configurations, and methods of use described in the context of one of the devices may be incorporated into any of the other devices. Furthermore, additional and alternative suitable components, features, configurations, and methods of using the devices, as well as various ways in which the teachings herein may be combined and interchanged, will be apparent to those of ordinary skill in the art in view of the teachings herein.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A biopsy device comprising:
    (a) a body;
    (b) a cannula extending distally from the body, wherein the cannula has a distal end and a lateral tissue receiving port positioned proximal to the distal end;
    (c) a cutter translatable relative to the cannula to sever tissue protruding through the lateral tissue receiving port;
    (d) a cutter actuation assembly configured to translate the cutter relative to the cannula; and
    (e) a valve assembly slidable in response to translation of the cutter, wherein the valve assembly is translatable distally from a proximal position to a first distal position, wherein the valve assembly is translatable further distally from the first distal position to a second distal position, wherein the valve assembly is configured to selectively communicate fluid to the cannula in the first distal position, wherein the valve assembly is configured to selectively vent the cannula to atmosphere in the second distal position.

2. The biopsy device of claim 1, wherein the valve assembly is configured to selectively seal the cannula in the proximal position.

3. The biopsy device of claim 1, wherein the biopsy device comprises a fluid pump.

4. The biopsy device of claim 1, wherein the cannula comprises a first lumen and a second lumen, wherein the cutter is configured to translate within the first lumen.

5. The biopsy device of claim 4, wherein the valve assembly is configured to selectively vent the second lumen to atmosphere.

6. The biopsy device of claim 1 further comprising a tissue sample holder, wherein the tissue sample holder is configured to hold the tissue severed by the cutter.

7. The biopsy device of claim 6, wherein the tissue sample holder is removably supported by the body of the biopsy device.

8. The biopsy device of claim 6, wherein the tissue sample holder comprises a vacuum port.

9. The biopsy device of claim 8 further comprising a vacuum source coupled with the vacuum port of the tissue sample holder, wherein the vacuum source is configured to provide vacuum to the cannula.

10. The biopsy device of claim 1 further comprising a motor, wherein the motor is operable to translate the cutter.

11. The biopsy device of claim 10, wherein the cutter is further configured to rotate relative to the cannula, wherein the motor is operable to rotate the cutter.

12. The biopsy device of claim 11 further comprising a vacuum source configured to provide vacuum to the cannula, wherein the motor is operable to actuate the vacuum source.

13. The biopsy device of claim 10, wherein the motor is positioned within the body of the biopsy device.

14. The biopsy device of claim 13 further comprising a power source positioned within the body of the biopsy device, wherein the power source is configured to provide power to the motor.

15. The biopsy device of claim 1, wherein the body comprises a probe portion and a holster portion, wherein the probe portion is selectively removable from the holster portion.

16. The biopsy device of claim 15, wherein the cutter actuation assembly is positioned within the holster portion, wherein the cutter is positioned within the probe portion.

17. A biopsy device comprising:
    (a) probe portion, wherein the probe portion comprises:
        (i) a cannula having a distal end and a lateral tissue receiving port positioned proximal to the distal end,
        (ii) a cutter translatable relative to the cannula to sever tissue protruding through the lateral tissue receiving port,
        (iii) a valve assembly translatable in response to translation of the cutter, wherein the valve assembly is translatable to selectively vent the cannula to atmosphere, and
        (iv) a fluid pump actuation assembly, wherein the fluid pump actuation assembly is operable to actuate a fluid pump to deliver fluid to the cannula; and
    (b) a holster portion removably couplable with the probe portion, wherein the holster portion comprises a motor operable to actuate the cutter, the valve assembly, and the fluid pump actuation assembly.

18. The biopsy device of claim 17, wherein the holster comprises a vacuum pump in fluid communication with the cannula.

19. The biopsy device of claim 18, wherein the motor is operable to actuate the vacuum pump.

20. A method of operating a biopsy device, wherein the biopsy device comprises a cannula having a lateral tissue receiving port, a cutter translatable relative to the cannula, and a valve assembly, the method comprising the steps of:
    (a) inserting the cannula within a patient;
    (b) prolapsing tissue within the lateral tissue receiving port;
    (c) translating the cutter distally to sever tissue received by the cannula;
    (d) translating the valve assembly distally to communicate a fluid to the cannula; and
    (e) continuing to translate the valve assembly distally to seal the cannula relative to the fluid and to communicate atmospheric air to the cannula.

* * * * *